(12) United States Patent
He et al.

(10) Patent No.: US 6,784,180 B2
(45) Date of Patent: Aug. 31, 2004

(54) PIPERIDINES DERIVATIVES AND THEIR USE AS SEROTONIN RECEPTOR ANTAGONISTS

(75) Inventors: John Xiaoqiang He, Fishers, IN (US); Nicholas Allan Honigschmidt, Brownburg, IN (US); Todd Jonathan Kohn, Fishers, IN (US); Vincent Patrick Rocco, Indianapolis, IN (US); Patrick Gianpietro Spinazze, Avon, IN (US); Kumiko Takeuchi, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/148,655

(22) PCT Filed: Dec. 6, 2000

(86) PCT No.: PCT/US00/32426

§ 371 (c)(1),
(2), (4) Date: Sep. 9, 2002

(87) PCT Pub. No.: WO01/46179

PCT Pub. Date: Jun. 28, 2001

(65) Prior Publication Data

US 2003/0225281 A1 Dec. 4, 2003

Related U.S. Application Data

(60) Provisional application No. 60/172,723, filed on Dec. 20, 1999.

(51) Int. Cl.[7] ............... C07D 409/04; A61K 31/445; A61P 25/34; A61P 25/24

(52) U.S. Cl. .............. 514/250; 546/202; 546/197; 546/201; 546/198; 546/199; 546/153; 546/79; 514/324; 514/321; 514/322; 514/323; 514/290; 514/312; 544/350

(58) Field of Search ................ 546/202, 197, 546/201, 198, 199, 153, 79; 514/324, 321, 322, 323, 250, 290, 312; 544/350

(56) References Cited

U.S. PATENT DOCUMENTS 5,741,789 A    4/1998   Hibschman et al. ........ 514/210

FOREIGN PATENT DOCUMENTS

| EP | 812826 | 12/1997 |
|----|--------|---------|
| EP | 814084 | 12/1997 |
| WO | WO95/33721 | 12/1995 |
| WO | 0976747 | * 2/2000 |

* cited by examiner

Primary Examiner—Richard L. Raymond
Assistant Examiner—Hong Liu
(74) Attorney, Agent, or Firm—Michael J. Sayles

(57) ABSTRACT

The present invention provides compounds of formula (I): which are useful for treating depression, anxiety, and alleviating the symptoms caused by withdrawal or partial withdrawal from the use of tobacco or of nicotine.

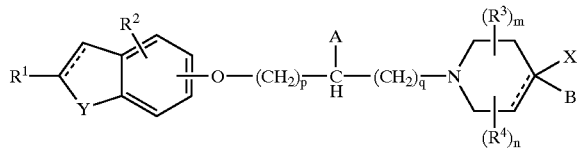

(I)

16 Claims, No Drawings

PIPERIDINES DERIVATIVES AND THEIR USE AS SEROTONIN RECEPTOR ANTAGONISTS

This application is a 371 of PCT/US00/32426 filed Dec. 6, 2000, which claims benefit of 60/172,723, filed Dec. 20, 1999.

Pharmaceutical researchers have discovered that the neurons of the brain which contain monoamines are of extreme importance in a great many physiological processes which affect many psychological and personality-affecting processes as well. In particular, serotonin (5-hydroxytryptamine; 5-HT) has been found to be a key to a very large number of processes which affect both physiological and psychological functions. Drugs which influence the function of serotonin in the brain are accordingly of great importance and are now used for a large number of different therapies.

The early generations of serotonin-affecting drugs tended to have a variety of different physiological functions, considered from both the mechanistic and therapeutic points of view. For example, many of the tricyclic antidepressant drugs are now known to be active as inhibitors of serotonin reuptake, and also to have anticholinergic, antihistaminic or anti-α-adrenergic activity. More recently, it has become possible to study the function of drugs at individual receptors in vitro or ex vivo, and it has also been realized that therapeutic agents free of extraneous mechanisms of action are advantageous to the patient.

The present invention provides compounds which have highly selective activity as antagonists and partial agonists of the serotonin $1_A$ receptor and a second activity as inhibitors of reuptake of serotonin. The best-known pharmaceutical with the latter efficacy is fluoxetine, and the importance of its use in the treatment of depression and other conditions is well documented and publicized. Artigas, TIPS, 14, 262 (1993), have suggested that the efficacy of a reuptake inhibitor may be decreased by the activation of serotonin $1_A$ receptors with the resultant reduction in the firing rate of serotonin neurons. Accordingly, present research in the central nervous system is focusing on the effect of combining reuptake inhibitors with compounds which affect the 5-$HT_{1A}$ receptor.

Compounds exhibiting both serotonin reuptake inhibition activity and 5-$HT_{1A}$ antagonist activity have been described, for example, in U.S. Pat. No. 5,576,321, issued Nov. 19, 1996. Compounds of the present invention are potent serotonin reuptake inhibitors and antagonists of the 5-$HT_{1A}$ receptor.

The present invention provides compounds of formula I:

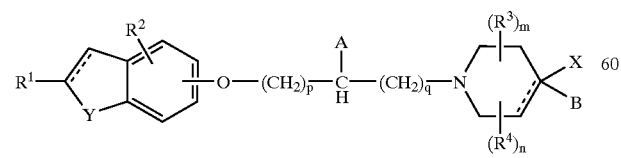

formula I wherein

A is hydrogen, OH or ($C_1$–$C_6$) alkoxy:

B is selected from the group consisting of:

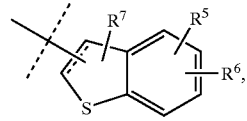
(a)

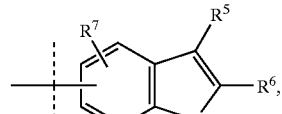
(b)

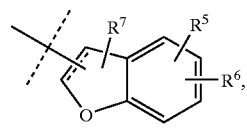
(c)

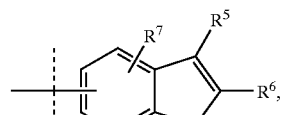
(d)

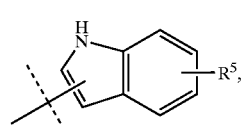
(e)

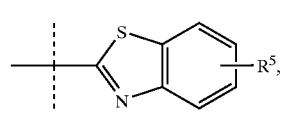
(f)

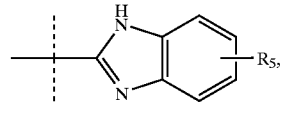
(g)

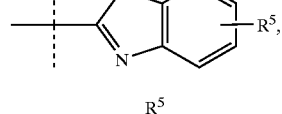
(h)

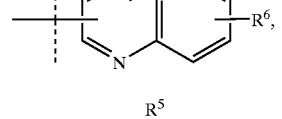
(i)

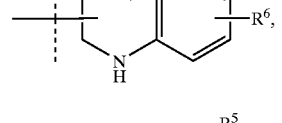
(j)

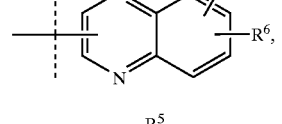
(k)

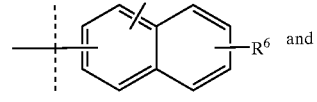
(l)

and

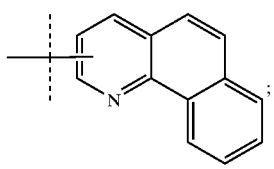
(m)

———represents a single or a double bond;

X is hydrogen, OH or $C_1$–$C_6$ alkoxy when ———represents a single bond in the piperidine ring, and X is nothing when ———represents a double bond in the piperidine ring;

Y is S or $CH_2$;

$R^1$ is hydrogen, F, $C_1$–$C_{20}$ alkyl, —C(=O)$NR^8R^9$, or CN;

$R^2$ is hydrogen, F, Cl, Br, I, OH, $C_1$–$C_6$ alkyl or $C_1$–$C_6$ alkoxy;

$R^3$ and $R^4$ are each independently hydrogen or $C_1$–$C_4$ alkyl;

$R^5$ and $R^6$ are each independently hydrogen, F, Cl, Br, I, OH, $C_1$–$C_6$ alkyl, $C_1$–$C_6$ alkoxy, halo($C_1$–$C_6$)alkyl, phenyl, —C(=O)$NR^8R^9$, $NO_2$, $NH_2$, CN, or phenyl substituted with from 1 to 3 substituents selected from the group consisting of F, Cl, Br, I, OH, $C_1$–$C_6$ alkyl, $C_1$–$C_6$ alkoxy, halo($C_1$–$C_6$) alkyl, $NO_2$, $NH_2$, CN, and phenyl;

$R^7$ is hydrogen, F, Cl, Br, I, OH, $C_1$–$C_6$ alkyl or ($C_1$–$C_6$ alkyl)$NR^8R^9$;

$R^8$ and $R^9$ are each independently hydrogen or $C_1$–$C_{10}$ alkyl;

m is 0, 1, or 2;

n is 0, 1, or 2;

p is 0, 1, 2, 3 or 4; and q is 0, 1, 2 or 3; or a pharmaceutically acceptable salt thereof.

The present invention further provides a method of inhibiting the reuptake of serotonin and antagonizing the 5-$HT_{1A}$ receptor which comprises administering to a patient an effective amount of a compound of formula I.

More particularly, the present invention provides a method for alleviating the symptoms caused by withdrawal or partial withdrawal from the use of tobacco or of nicotine; a method of treating anxiety; and a method of treating a condition chosen from the group consisting of depression, hypertension, cognitive disorders, Alzheimer's disease, psychosis, sleep disorders, gastric motility disorders, sexual dysfunction, brain trauma, memory loss, eating disorders and obesity, substance abuse, obsessive-compulsive disease, panic disorder, and migraine; which methods comprise administering to a patient an effective amount of a compound of formula I.

In addition, the present invention provides a method of potentiating the action of a serotonin reuptake inhibitor comprising administering to a patient an effective amount of a compound of formula I in combination with an effective amount of a serotonin reuptake inhibitor.

In addition, the invention provides pharmaceutical compositions of compounds of formula I, including the hydrates thereof, comprising, as an active ingredient, a compound of formula I in combination with a pharmaceutically acceptable carrier, diluent or excipient. This invention also encompasses novel intermediates, and processes for the synthesis of the compounds of formula I.

According to another aspect, the present invention provides the use of a compound of formula I, or a pharmaceutically acceptable salt thereof as defined hereinabove for the manufacture of a medicament for inhibiting the reuptake of serotonin and antagonizing the 5-$HT_{1A}$ receptor.

According to yet another aspect, the present invention provides the use of a compound of formula I or a pharmaceutically acceptable salt thereof as defined hereinabove for inhibiting the reuptake of serotonin and antagonizing the 5-$HT_{1A}$ receptor.

It is understood that the compounds of formula Ia:

formula Ia

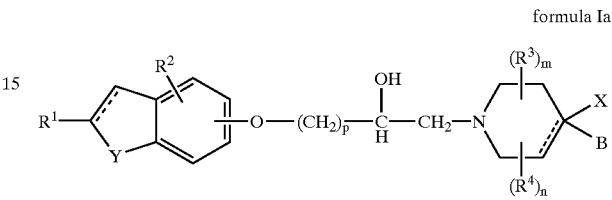

are included within the scope of the definition of formula I wherein the substituents are defined as hereinabove.

It is further understood that the compounds of the formula Iaa:

formula Iaa

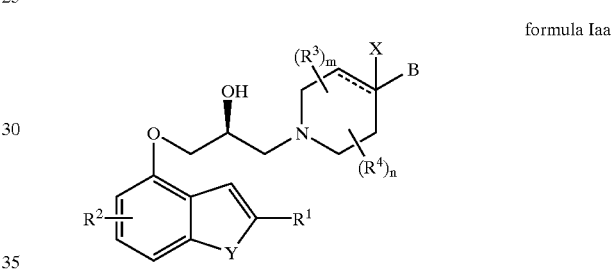

are included within the scope of the definition of formula I wherein the substituents are defined as hereinabove.

As used herein, the terms "Me", "Et", "Pr", "iPr", "Bu" and "t-Bu" refer to methyl, ethyl, propyl, isopropyl, butyl and tert-butyl, respectively.

As used herein, the terms "Halo", "Halide" or "Hal" refer to a chlorine, bromine, iodine or fluorine atom, unless otherwise specified herein.

As used herein the term "$C_1$–$C_4$ alkyl" refers to a straight or branched, monovalent, saturated aliphatic chain of 1 to 4 carbon atoms and includes, but is not limited to methyl, ethyl, n-propyl, isopropyl, n-butyl, isobutyl and the like.

As used herein the term "$C_1$–$C_6$ alkyl" refers to a straight or branched, monovalent, saturated aliphatic chain of 1 to 6 carbon atoms and includes, but is not limited to methyl, ethyl, n-propyl, isopropyl, n-butyl, isobutyl, t-butyl, n-pentyl, n-hexyl, and the like.

As used herein the term "$C_1$–$C_{10}$ alkyl" refers to a straight or branched, monovalent, saturated aliphatic chain of 1 to 10 carbon atoms and includes, but is not limited to methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like.

As used herein the term "$C_1$–$C_{20}$ alkyl" refers to a straight or branched, monovalent, saturated aliphatic chain of 1 to 20 carbon atoms and includes, but is not limited to, methyl, ethyl, propyl, isopropyl, butyl, isobutyl, t-butyl, pentyl, isopentyl, hexyl, 3-methylpentyl, 2-ethylbutyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-nonadecyl, n-eicosyl and the like.

As used herein the term "halo($C_1$–$C_6$)alkyl" refers to a straight or branched alkyl chain having from one to six carbon atoms with 1, 2 or 3 halogen atoms attached to it. Typical halo($C_1$–$C_6$)alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl and the like. The term "halo($C_1$–$C_6$)alkyl" includes within its definition the term "halo($C_1$–$C_4$)alkyl".

As used herein the term "$C_1$–$C_6$ alkoxy" refers to a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the term "$C_1$–$C_4$ alkoxy".

The designation "⁣⁣⁣⁣‖" refers to a bond that protrudes forward out of the plane of the page.

The designation "⁣⁣⁣⁣‖" refers to a bond that protrudes backward out of the plane of the page.

This invention includes the hydrates and the pharmaceutically acceptable salts of the compounds of formula I. A compound of this invention can possess a sufficiently basic functional group which can react with any of a number of inorganic and organic acids, to form a pharmaceutically acceptable salt.

The term "pharmaceutically acceptable salt" as used herein, refers to salts of the compounds of formula I which are substantially non-toxic to living organisms. Typical pharmaceutically acceptable salts include those salts prepared by reaction of the compounds of the present invention with a pharmaceutically acceptable mineral or organic acid. Such salts are also known as acid addition salts. Such salts include the pharmaceutically acceptable salts listed in *Journal of Pharmaceutical Science*, 66, 2–19 (1977) which are known to the skilled artisan.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprate, caprylate, acrylate, ascorbate, formate, hydrochloride, dihydrochloride, isobutyrate, caproate, heptanoate, propiolate, propionate, phenylpropionate, salicylate, oxalate, malonate, succinate, suberate, sebacate, fumarate, malate, maleate, hydroxymaleate, mandelate, nicotinate, isonicotinate, cinnamate, hippurate, nitrate, phthalate, teraphthalate, butyne-1,4-dioate, butyne-1,4-dicarboxylate, hexyne-1,4-dicarboxylate, hexyne-1,6-dioate, benzoate, chlorobenzoate, methylbenzoate, hydroxybenzoate, methoxybenzoate, dinitrobenzoate, o-acetoxybenzoate, naphthalene-2-benzoate, phthalate, p-toluenesulfonate, p-bromobenzenesulfonate, p-chlorobenzenesulfonate, xylenesulfonate, phenylacetate, trifluoroacetate, phenylpropionate, phenylbutyrate, citrate, lactate, α-hydroxybutyrate, glycolate, tartrate, benzenesulfonate, methanesulfonate, ethanesulfonate, propanesulfonate, hydroxyethanesulfonate, naphthalene-1-sulfonate, napthalene-2-sulfonate, mandelate, tartarate, and the like. Preferred pharmaceutically acceptable acid addition salts are those formed with mineral acids such as hydrochloric acid and hydrobromic acid, and those formed with organic acids such as maleic acid, oxalic acid and methanesulfonic acid.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that such salts may exist as a hydrate.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of formulas I or Ia can be resolved by one of ordinary skill in the art using standard techniques well known in the art, such as those described by J. Jacques, et al., "Enantiomers, Racemates, and Resolutions", John Wiley and Sons, Inc., 1981.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

The specific stereoisomers and enantiomers of compounds of formula (I) can be prepared by one of ordinary skill in the art utilizing well known techniques and processes, such as those disclosed by Eliel and Wilen, "Stereochemistry of Organic Compounds", John Wiley & Sons, Inc., 1994, Chapter 7, Separation of Stereoisomers. Resolution. Racemization, and by Collet and Wilen, "Enantiomers, Racemates, and Resolutions", John Wiley & Sons, Inc., 1981. For example, the specific stereoisomers and enantiomers can be prepared by stereospecific syntheses using enantiomerically and geometrically pure, or enantiomerically or geometrically enriched starting materials. In addition, the specific stereoisomers and enantiomers can be resolved and recovered by techniques such as chromatography on chiral stationary phases, enzymatic resolution or fractional recrystallization of addition salts formed by reagents used for that purpose.

As used herein, the term "SRI" refers to serotonin reuptake inhibitor.

As used herein the term "serotonin" is equivalent to and interchangeable with the terms "5-HT" or "5-hydroxytryptamine".

As used herein, "Pg" refers to a protecting group on the amine which is commonly employed to block or protect the amine while reacting other functional groups on the compound. Examples of protecting groups (Pg) used to protect the amino group and their preparation are disclosed by T. W. Greene, "Protective Groups in Organic Synthesis," John Wiley & Sons, 1981, pages 218–287. Choice of the protecting group used will depend upon the substituent to be protected and the conditions that will be employed in subsequent reaction steps wherein protection is required, and is well within the knowledge of one of ordinary skill in the art. Preferred protecting groups are t-butoxycarbonyl also known as the BOC protecting group, and benzyloxycarbonyl.

The compounds of formula I can be prepared by techniques and procedures readily available to one of ordinary skill in the art. For example, various starting materials and general procedures which may be employed by one of ordinary skill in the art in the preparation of compounds of formula I are described in U.S. Pat. No. 3,929,793, issued Dec. 30, 1975, U.S. Pat. No. 4,304,915, issued Dec. 8, 1981, U.S. Pat. No. 4,288,442, issued Sep. 8, 1981, U.S. Pat. No. 4,361,562, issued Nov. 30, 1982, U.S. Pat. No. 4,460,586, issued Jul. 17, 1984, U.S. Pat. No. 4,704,390, issued Nov. 3, 1987, U.S. Pat. No. 4,935,414, issued Jun. 19, 1990, U.S. Pat. No. 5,013,761, issued May 7, 1991, and U.S. Pat. No. 5,614,523, issued Mar. 25, 1997. More specifically, compounds of formula I can be prepared by following the procedures as set forth in Schemes I through IV. All substituents, unless otherwise indicated, are previously defined. The reagents and starting materials are readily available to one of ordinary skill in the art. More specifically, Schemes I through II provide general syntheses of various intermediate piperidines.

Scheme I

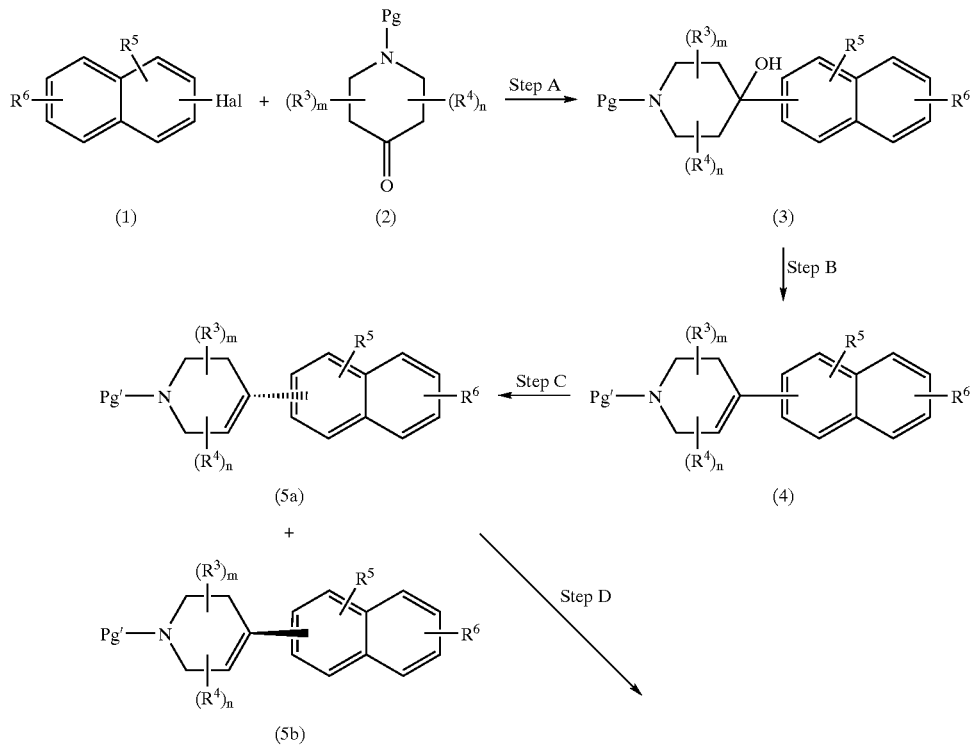

-continued

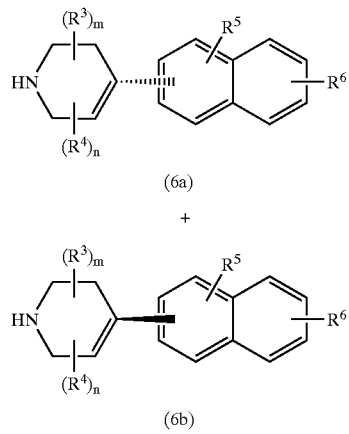

(6a)

+

(6b)

Pg' = hydrogen or a protecting group

In Scheme I, step A, compound (1) is added to piperidone (2) under conditions well known in the art, to provide the alcohol (3). For example, an appropriately substituted naphthalene, such as 2-bromonaphthalene, 1-bromo-5-methoxy-naphthalene, 2-bromo-7-methoxy-naphthalene, 6-iodo-1-methoxy-naphthalene, and the like, is dissolved in a suitable organic solvent, such as tetrahydrofuran and cooled to about −78° C. To this stirring solution is added an excess of a suitable base, such as t-butyllithium. The mixture is stirred for about 1 to 3 hours, and 1.0 to about 1.1 equivalents of the piperidone (2) are added. The reaction is allowed to warm to room temperature and the alcohol (3) is isolated and purified by techniques well known in the art. For example, the mixture is diluted with water and extracted with a suitable organic solvent, such as ethyl acetate. The organic extracts are combined, washed with brine, dried over anhydrous sodium sulfate, filtered and concentrated under vacuum. The crude alcohol can then be purified by flash chromatography on silica gel with a suitable eluent, such as ethyl acetate/hexane to provide the purified alcohol (3). Alternatively, the crude isolated alcohol (3) can be carried directly onto the next step.

The piperidones (2) are readily available to one of ordinary skill in the art utilizing known starting materials. For example, I.V. Micovic, et al., *J. Chem. Soc., Perkin Trans.*, 1(16), 2041–2050 (1996) teach the preparation of variously substituted piperidine-2,4-diones. Such piperidine-2,4-diones can be selectively protected, alkylated, and reduced under conditions well known in the art to provide the desired piperidone (2). For example, compounds of the formula (2a')

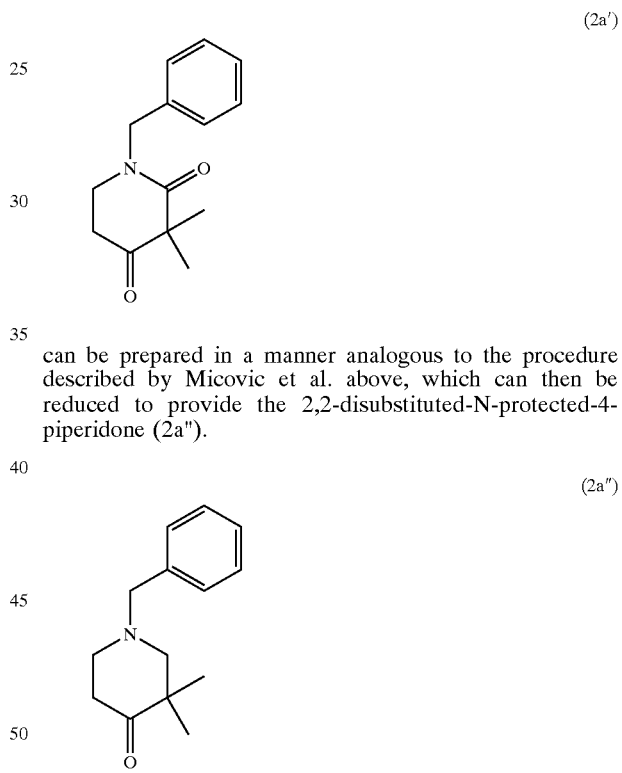

can be prepared in a manner analogous to the procedure described by Micovic et al. above, which can then be reduced to provide the 2,2-disubstituted-N-protected-4-piperidone (2a'').

In Scheme I, step B, the alcohol (3) is dehydrated under standard conditions to provide the 1,2,5,6-tetrahydropiperidine (4) wherein Pg' is maintained as a protecting group and does not represent hydrogen. For example, the alcohol (3) is dissolved in a suitable organic solvent, such as toluene, and treated with an excess of a suitable acid, such a p-toluenesulfonic acid monohydrate. The reaction mixture is heated at reflux for about 6 to 12 hours and then cooled. The 1,2,5,6-tetrahydropiperidine is then isolated and purified under conditions well known in the art. For example, the cooled reaction mixture is basified with 2 N sodium hydroxide and extracted with a suitable organic solvent, such as ethyl acetate. The organic extracts are combined, washed with brine, dried over anhydrous sodium sulfate, filtered and concentrated under vacuum. The crude residue is then purified by flash chromatography on silica gel with a suitable eluent, such as methanol/methylene chloride to provide the purified 1,2,5,6-tetrahydropiperidine (4).

Alternatively, in Scheme I, step B the alcohol (3) can be dehydrated and deprotected concomitantly under standard conditions to provide the compound (4) wherein Pg' is hydrogen. For example, alcohol (3) wherein the protecting group is N-t-butoxycarbonyl, is dissolved in a suitable organic solvent, such as dry dichloromethane and the solution is cooled to about 0° C. To this solution is added excess trifluoroacetic acid and the reaction mixture is stirred at about 0° C. for about 15 h. The reaction is then quenched at room temperature with saturated aqueous $NaHCO_3$ solution. The product is then isolated by techniques well known in the art, such as extraction, and then purified by flash chromatography. For example, the mixture is extracted with a suitable organic solvent, such as dichloromethane, the combined organic extracts are dried over anhydrous magnesium sulfate, filtered and concentrated under vacuum to provide the crude compound (4). This material can be purified by flash chromatography on silica gel with a suitable eluent, such as ethyl acetate/hexane.

In Scheme I, step C, the 1,2,5,6-tetrahydropiperidine (4) is hydrogenated under conditions well known in the art to provide a mixture of piperidines (5a) and (5b). For example, the 1,2,5,6-tetrahydropiperidine (4) is dissolved in a suitable organic solvent, such as ethanol and treated with a suitable catalyst, such as 5% palladium on carbon. The mixture is then placed under an atmosphere of hydrogen and stirred for about 12 hours at room temperature. The reaction mixture is then filtered to remove the catalyst and the filtrate is concentrated under vacuum to provide a mixture of isomers (5a) and (5b). It is readily appreciated by one of ordinary skill in the art that various isomers may exist at this step wherein the R groups can be either cis or trans to the naphthyl group. It is further recognized that these isomers may be separated from one another by techniques well known in the art, such as flash chromatography, radial chromatography or high performance liquid chromatography on silica gel with a suitable eluent, such as methanol/methylene chloride. Alternatively, the mixture of isomers may be carried on to the next step or the separated isomers may individually be carried on to the next step.

In Scheme I, step D, wherein Pg' is a protecting group and not hydrogen, the piperidines (5a) and (5b) are deprotected under conditions well known to one of ordinary skill in the art to provide piperidines (6a) and (6b). For example, when Pg is a methyl group, the piperidines (5a) and (5b) are dissolved in a suitable organic solvent, such as dichloroethane and cooled to about 0° C. The cooled solution is then treated with an excess of 1-chloroethylchloroformate. The reaction is then allowed to warm to room temperature and then heated at reflux for about 12 hours. After cooling, the solvent is then removed under vacuum and the residue is dissolved in a suitable organic solvent, such as methanol. The solution is then heated at reflux for about 2 to 4 hours, cooled to room temperature, and then concentrated under vacuum. The residue is treated with water and a suitable organic solvent, such as ethyl acetate. The phases are separated and the aqueous phase is extracted with ethyl acetate. The organic extracts, including the first organic phase, are combined, rinsed with brine, dried over anhydrous sodium sulfate, filtered and concentrated under vacuum to provide the crude piperidines (6a) and (6b). The mixture can then be separated into purified individual stereoisomers if they were not already separated in step C using similar techniques, such as flash chromatography, radial chromatography or high performance chromatography on silica gel with a suitable eluent, such as methanol/methylene chloride.

It is readily appreciated by one of ordinary skill in the art that the sequence of steps of dehydration, deprotection, and reduction can be varied depending upon the protecting groups utilized and the ultimate products desired. The conditions required for varying the sequence are well within the knowledge of one of ordinary skill in the art.

Scheme IA

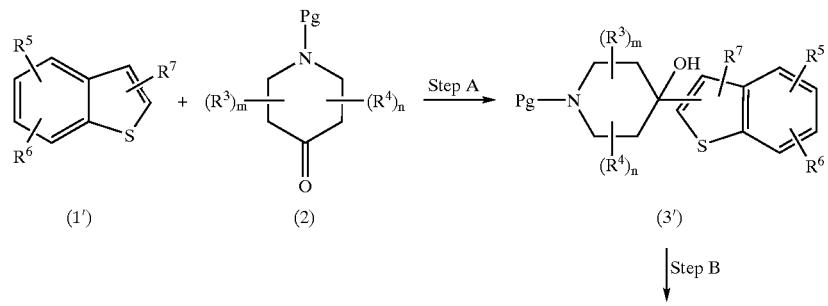

-continued

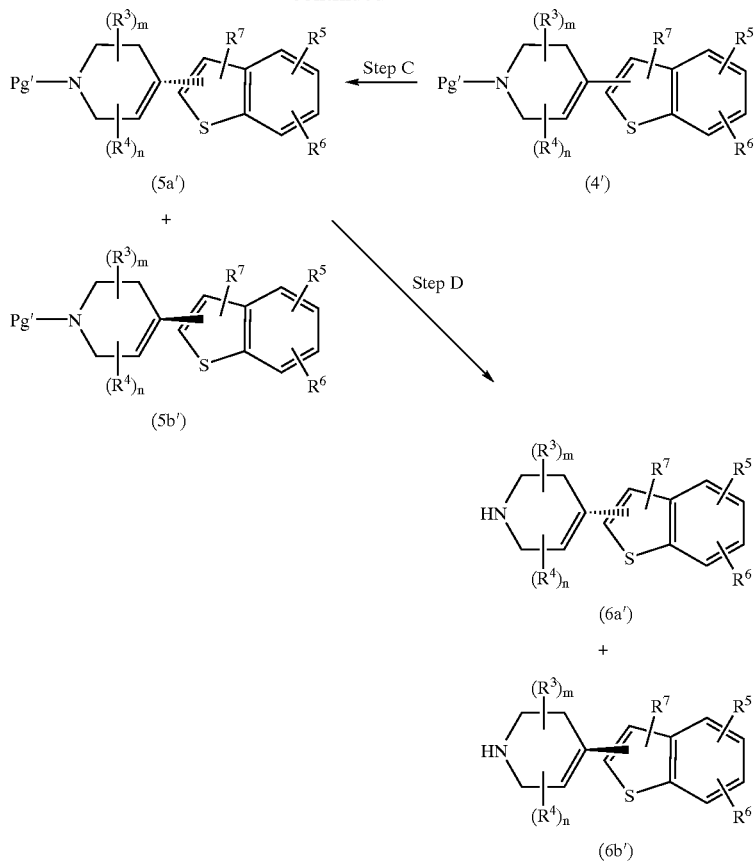

In Scheme IA, the steps A through D are carried out in a manner analogous to the procedures set forth in Scheme I, steps A through D respectively.

Scheme IB

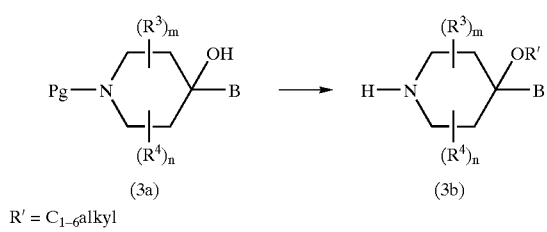

R' = C$_{1-6}$alkyl

In Scheme IB, alcohol (3a) is alkylated under standard conditions to provide the ether (3b). For example, alcohol (3a), wherein the protecting group is N-t-butoxycarbonyl, is dissolved in a suitable organic solvent, such as dry MeOH and the solution is cooled to about 0° C. To this solution is added excess trifluoroacetic acid. The reaction mixture is then stirred at room temperature for about one to 6 days. The reaction is then quenched at room temperature with saturated aqueous NaHCO$_3$ solution, extracted with a suitable organic solvent such as dichloromethane, the combined organic extracts are dried over anhydrous magnesium sulfate, filtered and concentrated under vacuum to provide the crude ether (3b). The crude ether (3b) can then be purified by flash chromatography on silica gel with a suitable eluent, such as 7% (10% conc. NH$_4$OH in MeOH)/CH$_2$Cl$_2$.

Scheme IC

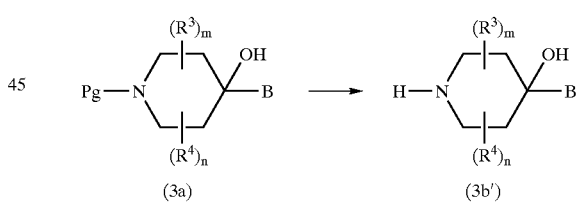

In Scheme IC, alcohol (3a) can be deprotected without dehydration under standard conditions well known in the art, through appropriate choice of protecting groups, to provide the deprotected alcohol (3b'). For example, the alcohol (3a), wherein the protecting group is a —CH$_2$CH═CH$_2$ group, is dissolved in a suitable solvent, such as aqueous ethanol (10% H$_2$O). The solution is then treated with chlorotris(triphenylphosphine) rhodium(I) (Wilkinson's catalyst) and approximately 50% of the solvent is then distilled off over a period of about 1 hour. An additional 65 mL of solvent and 45 mg of Wilkinson's catalyst is added and the reaction mixture is refluxed for about 1 hour and then the solvent is again distilled off to about 50% volume. The reaction mixture is then evaporated and the residue is purified using silica gel chromatography with a suitable eluent, such as dichloromethane/20% methanol, 2% anhydrous ammonia in dichloromethane gradient, to provide the purified deprotected alcohol (3b').

art that various isomers may exist at this particular step wherein the R groups can be either cis or trans to the naphthyl group. It is further recognized that these isomers may be separated from one another by techniques well known in the art, such as flash chromatography, radial

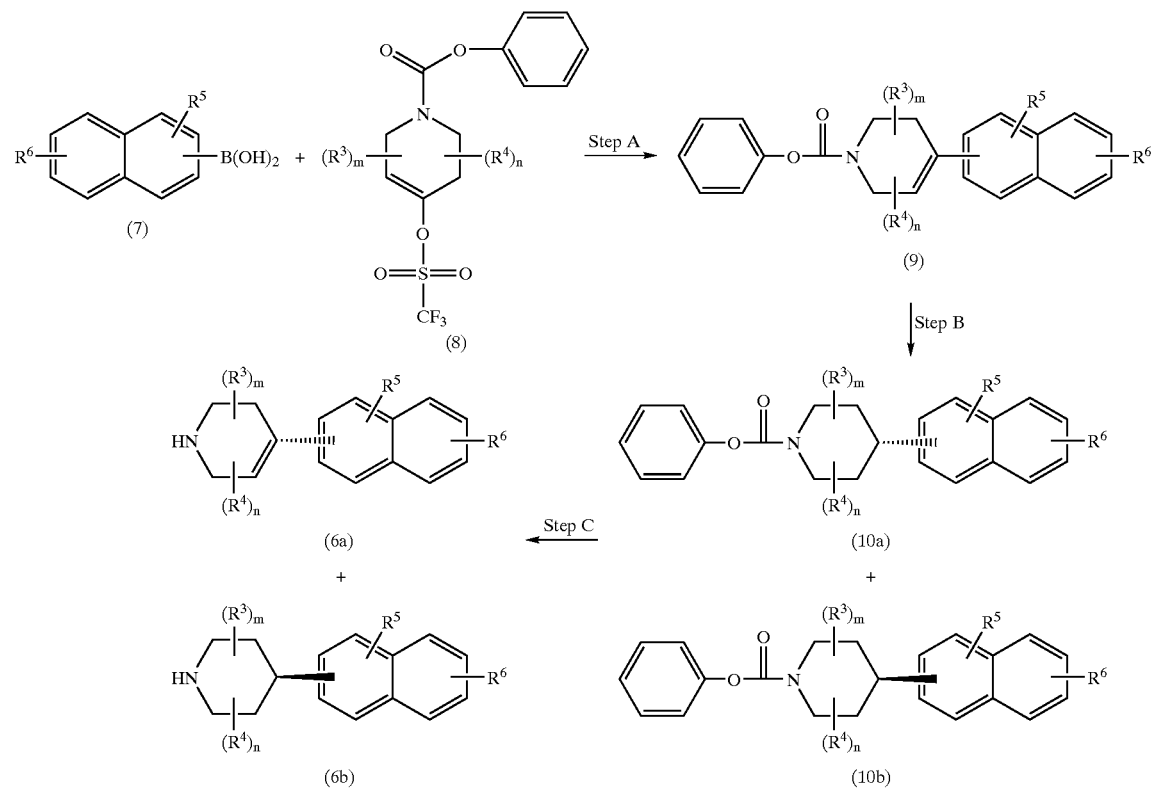

Scheme II

In Scheme II, step A, a naphthylboronic acid (7), such as 2-naphthylboronic acid is combined with the 1,2,5,6-tetrahydropiperidine (8) to provide the coupled compound (9). For example, about 1 to 1.5 equivalents of a naphthylboronic acid (7) is combined with about 1 equivalent of 1,2,5,6-tetrahydropiperidine (8), about 2 equivalents of lithium chloride, a catalytic amount of tetrakis(triphenylphosphine)palladium(0) in a mixture of 2 M aqueous sodium carbonate and tetrahydrofuran. The mixture is heated at reflux for about 12 hours and then cooled to room temperature. The reaction is then treated with 2 N sodium hydroxide and extracted with a suitable organic solvent, such as ethyl acetate. The organic extracts are combined, rinsed with brine, dried over anhydrous sodium sulfate, filtered and concentrated under vacuum. The crude residue is then purified by flash chromatography on silica gel with a suitable eluent such as ethyl acetate/hexane to provide the compound (9).

In Scheme II, step B, compound 9 is hydrogenated under standard conditions to provide the piperidines (10a) and (10b). For example, compound (9) is dissolved in a suitable organic solvent, such as methanol, treated with a suitable catalyst, such as 5% palladium on carbon and stirred under an atmosphere of hydrogen for about 12 hours at room temperature. The reaction mixture is then filtered to remove the catalyst and the filtrate is concentrated under vacuum to provide piperidines (10a) and (10b). As noted in Scheme I, step C, it is readily appreciated by one of ordinary skill in the chromatography or high performance liquid chromatography on silica gel with a suitable eluent, such as methanol/methylene chloride. Alternatively, the mixture of isomers may be carried on to the next step or the separated isomers may individually be carried onto the next step.

In Scheme II, step C, the piperidines (10a) and (10b) are deprotected under conditions well known in the art to provide the piperidines (6a) and (6b). For example, piperidines (10a) and (10b) are dissolved in a suitable solvent mixture, such as 50% water/isopropanol and treated with an excess of a suitable base, such as potassium hydroxide. The reaction mixture is then heated at reflux for about 1 to 3 days and then cooled to room temperature. 2 N sodium hydroxide is added and the reaction is extracted with a suitable organic solvent, such as ethyl acetate. The organic extracts are combined, rinsed with brine, dried over anhydrous sodium sulfate, filtered and concentrated under vacuum. The crude residue is then purified by flash chromatography on silica gel with a suitable eluent, such as methanol/methylene chloride to provide the purified piperidines (6a) and (6b). The mixture can then be separated into individual stereoisomers if they were not already separated in step C using similar techniques, such as flash chromatography, radial chromatography or high performance chromatography on silica gel with a suitable eluent, such as methanol/methylene chloride.

It is readily appreciated by one of ordinary skill in the art that compounds (4), (4') and (9) can be deprotected prior to reduction and the unsaturated deprotected piperidines can be used directly in Schemes III and IV.

Scheme IIA

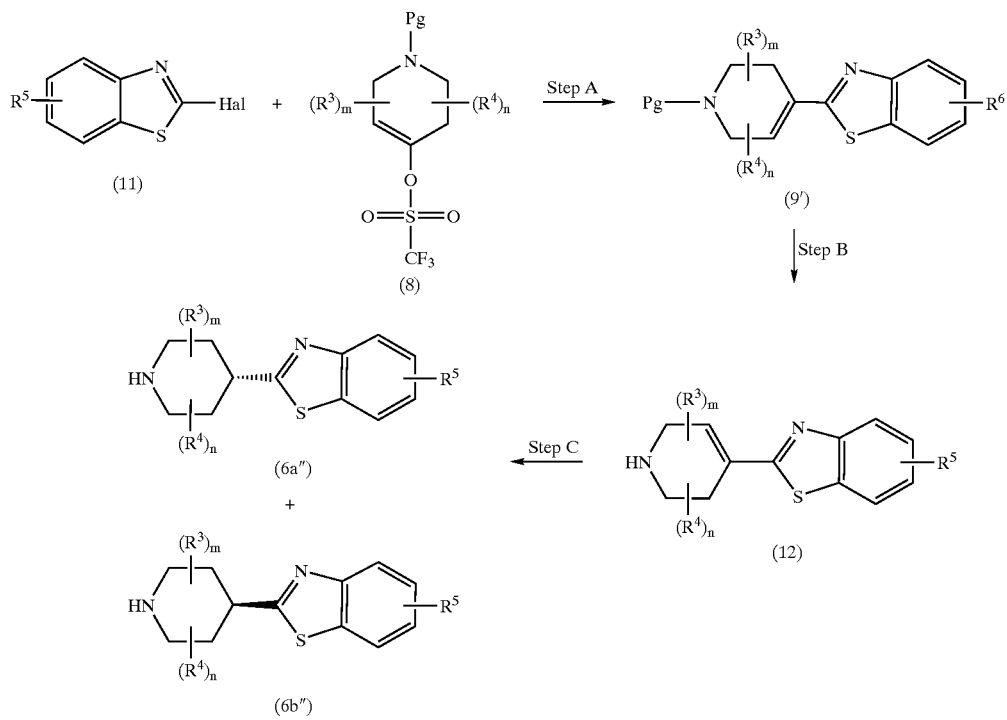

In Scheme IIA, step A, a 2-halo-benzothiazole (11), such as 2-chloro-4-fluorobenzothiazole, is combined with the 1,2,5,6-tetrahydropiperidine (8), to provide the coupled compound (9'). For example, about 1 equivalent of a 2-halo-benzothiazole (11) is combined with about 1.2 equivalents of 1,2,5,6-tetrahydropiperidine (8), about 1 equivalent of bis(trimethyltin), about 3 equivalents of lithium chloride, and a catalytic amount of tetrakis(triphenylphosphine) palladium(0) in a suitable organic solvent, such as 1,4-dioxane. The mixture is heated at reflux for about 20 hours and then cooled to about 20° C. The reaction is then treated with saturated potassium fluoride and ethyl acetate, and stirred for about 2 hours. The organic phase is separated, washed with brine, dried over anhydrous sodium sulfate, filtered and concentrated under vacuum. The crude residue is then purified by flash chromatography on silica gel with a suitable eluent such as ethyl acetate/hexane to provide the compound (9').

In Scheme IIA, Step B, compound (9') is deprotected under standard conditions to provide compound (12). For example, compound (9') is dissolved in a suitable organic solvent, such as dichloromethane, cooled to about 0° C. and treated with an excess of trifluoroacetic acid. The mixture is then stirred for about 30 minutes, then warmed to about 20° C. and stirred for an additional 20 minutes. The mixture is then diluted with 2 N sodium hydroxide and extracted with a suitable organic solvent, such as ethyl acetate. The organic extracts are combined, dried over anhydrous sodium sulfate, filtered and concentrated under vacuum to provide the crude compound (12). Compound (12) can then be purified by flash chromatography on silica gel with a suitable eluent, such as (dichloromethane/10% methanol 1% ammonium hydroxide in dichloromethane gradient elution) to provide the purified compound (12).

In Scheme IIA, step C, compound (12) is hydrogenated under standard conditions to provide the cis and trans isomers (6a") and (6b"). For example, compound (12) is dissolved in a suitable organic solvent, such as ethanol and treated with a catalytic amount of platinum oxide. The mixture is then hydrogenated under 1 atmosphere for about 20 hours, filtered and the filtrate concentrated under vacuum to provide the cis and trans isomers (6a") and (6b"). The compounds can then be separated using standard techniques well known to one of ordinary skill in the art, such as recrystallization techniques, flash chromatography or chiral chromatography.

It is readily appreciated by one of ordinary skill in the art that piperidines of structure (16) [see Schemes III and IV below], wherein B represents:

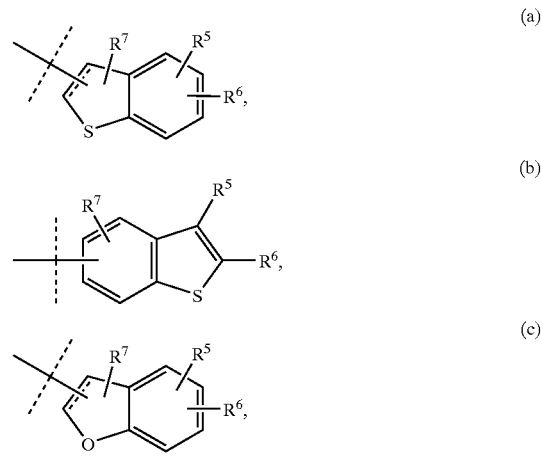

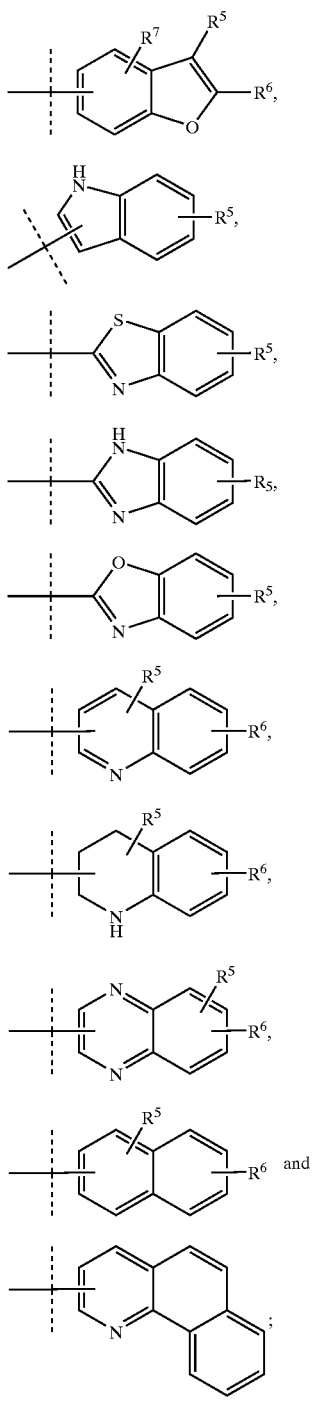

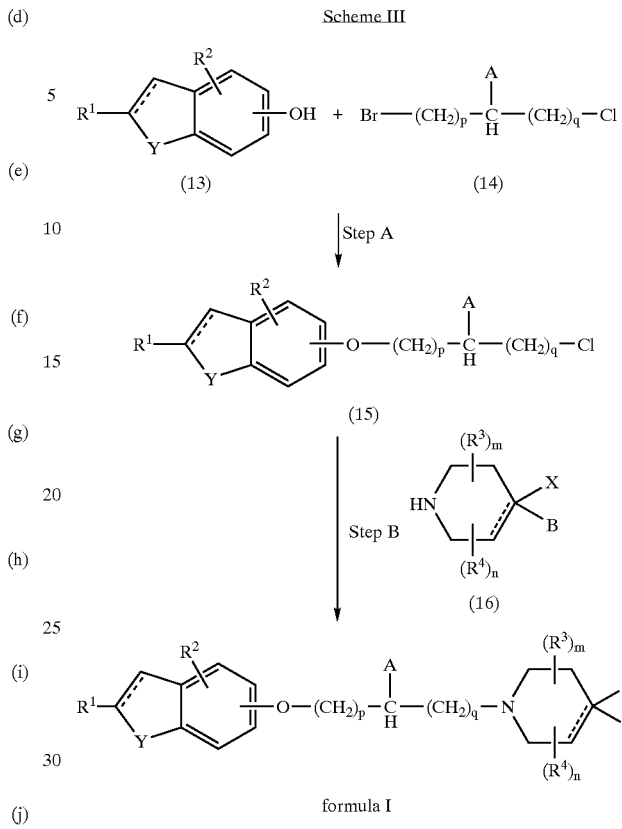

Scheme III formula I

In Scheme III, step A, compound (13) is coupled with compound (14) under standard conditions well known in the art, to provide compound (15). For example, compound (13) is dissolved in a suitable organic solvent, such as DMF, and treated with about one equivalent of a suitable base, such as sodium hydride. To the stirring solution is added about 1.1 equivalents of compound (14) and the reaction is stirred at about −10° C. to room temperature for about 20 minutes to 1 hour. Compound (15) is then isolated and purified by techniques well known in the art, such as extraction techniques and flash chromatography. For example, the reaction mixture is diluted with water and extracted with a suitable organic solvent, such as ethyl acetate. The organic extracts are combined, dried over anhydrous magnesium sulfate, filtered and concentrated under vacuum to provide the crude material. The crude material can be purified by flash chromatography on silica gel with a suitable eluent, such as ethyl acetate/hexane.

In Scheme III, step B compound (15) is coupled with piperidine (16) under standard conditions well known in the art to provide the compound of formula I. For example, compound (15) is dissolved in a suitable organic solvent, such as dimethylformamide with about one equivalent of a suitable neutralizing agent, such as sodium bicarbonate. To this mixture is added about one equivalent of a piperidine (16) and the mixture is heated at about 70° C. to 90° C. for about 4 hours to 12 hours. The compound of formula I is then isolated and purified by techniques well known in the art, such as extraction techniques and flash chromatography. For example, the reaction mixture is diluted with water and extracted with a suitable organic solvent, such as ethyl acetate. The organic extracts are combined, washed with water and brine, dried over anhydrous magnesium sulfate, filtered and concentrated under vacuum to provide the crude can be prepared under standard conditions, such as in a manner analogous to the procedures set forth in Schemes I through IIA for preparation of the piperidines described therein.

Compounds of formula I are prepared following generally the procedure set forth in Scheme III. All substituents, unless otherwise indicated, are previously defined. The reagents and starting materials are readily available to one of ordinary skill in the art.

material. The crude material can be purified by flash chromatography on silica gel with a suitable eluent, such as ethyl acetate/hexane.

Compounds of formula Ia are prepared following generally the procedure set forth in Scheme IV. All substituents, unless otherwise indicated, are previously defined. The reagents and starting materials are readily available to one of ordinary skill in the art.

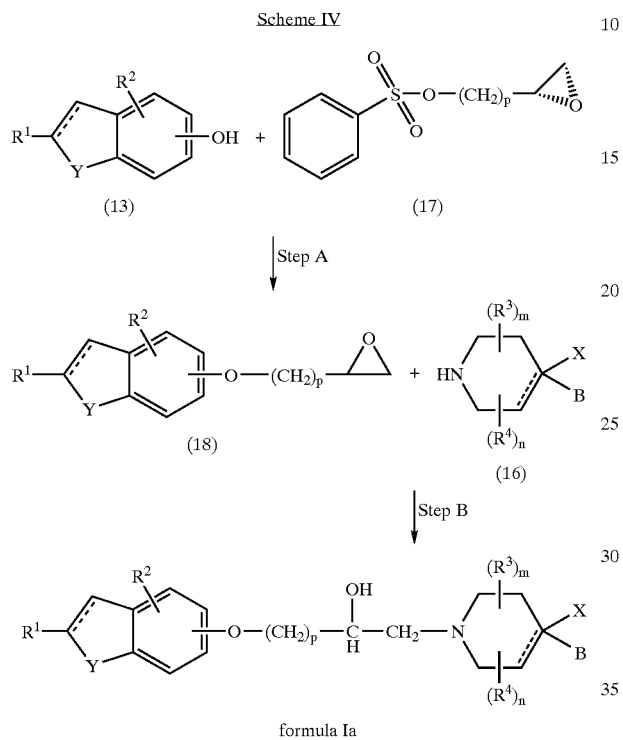

In Scheme IV, step A, the compound of structure (13) is coupled with the epoxide (17) to provide the epoxide (18). For example, compound (13) is dissolved in a suitable organic solvent, such as dimethylformamide and cooled to 0° C. About 1.1 equivalents of sodium hydride is added to the solution which is then stirred for about one hour. A solution of one equivalent of the epoxide (17) in dimethylformamide is then added dropwise to the solution. The reaction mixture is then stirred for about 1 to 24 hours at 0° C. It is then quenched with water. The resulting solution is extracted with a suitable organic solvent, such as ethyl acetate. The organic layers are combined, washed with water, dried over anhydrous magnesium sulfate, filtered and concentrated to provide crude epoxide (18). The crude product can be purified by crystallization with a suitable solvent, such as dichloromethane or by flash chromatography on silica gel with a suitable eluent, such as dichloromethane/hexane.

In Scheme IV, step B, the epoxide (18) is opened with the substituted piperidine of structure (16) under standard conditions well known in the art, such as those disclosed by Krushinski, et al. in U.S. Pat. No. 5,576,321, issued Nov. 19, 1996, to provide the compound of formula Ia. For example, epoxide (18), such as (S)-(+)-4-(oxiranylmethoxy)-1H-indole is dissolved in a suitable organic solvent, such as methanol, and treated with about one equivalent of piperidine (16). The solution is then heated to reflux for about 8 to 12 hours and then cooled to room temperature. The reaction mixture is then concentrated under vacuum and the crude residue is purified and resulting stereoisomers separated from each other by techniques well known in the art, such as flash chromatography, radial chromatography or high performance liquid chromatography on silica gel with a suitable eluent, such as methanol/methylene chloride.

The following examples are illustrative only and represent typical syntheses of the compounds of formula I and formula Ia as described generally above. The reagents and starting materials are readily available to one of ordinary skill in the art. As used herein, the following terms have the meanings indicated: "eq" or "equiv." refers to equivalents; "g" refers to grams; "mg" refers to milligrams; "L" refers to liters; "mL" refers to milliliters; "µL" refers to microliters; "mol" refers to moles; "mmol" refers to millimoles; "psi" refers to pounds per square inch; "min" refers to minutes; "h" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ"refers to parts per million down-field from tetramethylsilane; "THF" refers to tetrahydrofuran; "DMF" refers to N,N-dimethylformamide; "DMSO" refers to methyl sulfoxide; "LDA" refers to lithium diisopropylamide; "aq" refers to aqueous; "EtOAc" refers to ethyl acetate; "iPrOAc" refers to isopropyl acetate; "MeOH" refers to methanol; "MTBE" refers to tert-butyl methyl ether, and "RT" refers to room temperature.

Preparation 1

Preparation of 1-Bromo-5-methoxy-naphthalene.

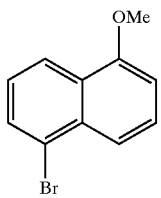

Preparation of 5-Bromo-3,4-dihydro-1(2H)-naphthalenone and 7-Bromo-3,4-dihydro-1(2H)-naphthalenone.

Anhydrous $AlCl_3$ (66.67 g, 0.50 mol, 99.99%) under $N_2$ was stirred vigorously as 1-tetralone (29.83 g, 0.20 mol) was added dropwise over ~7 min. The evolved HCl gas was scrubbed through 5 N NaOH. The resulting mixture was a dark brown oil that exothermed to 75° C. When the temperature had cooled to 50° C., $Br_2$ was added dropwise over 15 min. The mixture, which had cooled further to 40° C., was heated to 80° C. for 5 min, then poured into a mixture of ice (600 g) and 12 N HCl (80 mL). All the ice melted, leaving a cool dark mixture which was diluted with $H_2O$ (200 mL) and extracted with $CH_2Cl_2$ (200 mL, 100 mL). The combined extracts were dried with $MgSO_4$ and concentrated in vacuo (30–60° C.) to a dark brown oil (45.6 g; theory=45.02 g).

Chromatography over silica gel 60 with 8:1 heptane:THF did not prove effective, but two passes through the Biotage radially pressured silica gel cartridges using 9:1 heptane:MTBE as eluent produced acceptably pure fractions.

5-Bromo-3,4-dihydro-1(2H)-naphthalenone was isolated as an orange oil (12.27 g, 28.3%). HPLC showed an apparent wide divergence in absorbances at 230 nm for the two regioisomers, and was therefore not reliable for a potency check. TLC on silica gel (4:1 heptane:MTBE) confirmed modest contamination with 7-bromo-3,4-dihydro-1(2H)-naphthalenone.

7-Bromo-3,4-dihydro-1(2H)-naphthalenone was isolated as a yellowish-white solid (15.48 g, 35.8%); mp 69.5–75° C.

(lit 74–75° C.). ¹H NMR (CDCl₃) corresponded to the literature description, plus a trace of heptane and an undefined by-product. TLC showed it to be cleaner than 5-bromo-3,4-dihydro-1(2H)-naphthalenone.

A third fraction of orange oil (9.06 g, 20.9%) was isolated. TLC showed it to be a nearly 1:1 ratio of 5-bromo-3,4-dihydro-1(2H)-Naphthalenone, and 7-bromo-3,4-dihydro-1(2H)-Naphthalenone.

Preparation of 2,5-Dibromo-3,4-dihydro-1(2H)-naphthalenone.

A clear yellow solution of 5-bromo-3,4-dihydro-1(2H)-Naphthalenone(12.09 g, 53.7 mmol) in freshly opened Et₂O (220 mL) under an N₂ atmosphere was chilled to −5° C. HCl was bubbled in subsurface for 1 min, causing no visible change. The dropwise addition of a solution of Br₂ (8.58 g, 53.7 mmol) in CH₂Cl₂ (20 mL) and Et₂O (2 mL) to the vigorously stirring solution of 5-bromo-3,4-dihydro-1(2H)-naphthalenone over 2 h (each drop was allowed to fully decolorize before adding the next) produced a product mixture that assayed by HPLC. Peak area showed 79.4% title compound, 9.5% unreacted 5-bromo-3,4-dihydro-1(2H)-naphthalenone, 0.6% unidentified, and 9.4% 2,2,5-tribromo-1-tetralone. The addition of H₂O produced a top light brown organic phase, and a clear, colorless bottom aqueous phase which was separated. After drying with MgSO₄, the organic layer was concentrated in vacuo at room temperature to give the crude intermediate title compound as a light brown oil (16.08 g, 98.5%).

Preparation of 5-Bromo-1-naphthalenol.

The crude mixture of 2,5-dibromo-1-tetralone (16.08 g, 52.9 mmol,), LiCl (5.61 g, 132 mmol), and 120 mL of dry DMF were combined under an N₂ atmosphere and heated to reflux (~155° C.). The mixture turned dark brown. HPLC showed complete consumption of the starting material in just 0.5 h. After cooling to room temperature, the mixture was diluted with 1 N HCl (200 mL) and extracted three times with Et₂O (100 mL, 25 mL, 25 mL). The Et₂O layers were combined to give a brown hazy mixture (some emulsion). After stirring with decolorizing carbon (10 g, Calgon ADP) and filtration through hyflo supercel, a clear light yellow solution was obtained. This solution was extracted with 3 N NaOH (100 mL, 25 mL), leaving the non-naphtholic byproducts behind. The brown NaOH extracts were combined, acidified to pH 1 with conc. HCl, and extracted with CH₂Cl₂ (100 mL, 25 mL). The combined CH₂Cl₂ layers formed a deep red solution. After stirring with decolorizing carbon (5 g, Darco G-60) and filtration through hyflo supercel, the solution was again light yellow. An equal volume of heptane was added, and the CH₂Cl₂ was distilled away. When the temperature reached 75° C., gray precipitate became evident. This increased substantially on cooling to room temperature. Following filtration and drying in vacuo at 50° C., a product mixture of gray solid (5.92 g, 50.2%) was obtained. HPLC showed this to be a mixture of 7-bromo-1-naphthol (48.3%) and 5-bromo-1-naphthol (50.8%). However, ¹H NMR (CDCl₃) integration showed that the actual ratio was about 9/1 5-Br/7-Br. Preparative reverse phase HPLC gave one peak of 5-bromo-1-naphthol as a white solid (3.22 g, 27.3%).

Preparation of the Final Title Compound.

Purified 5-bromo-1-naphthol (3.22 g, 14.4 mmol), was dissolved in CH₃CN (50 mL), giving a clear and nearly colorless solution. Dimethylsulfate (2.72 g, 21.6 mmol, 1.5 equiv), K₂CO₃ (3.0 g, 21.6 mmol), and tetrabutylammonium bromide (TBAB, 20 mg) as phase transfer catalyst were added, and the resulting mixture was stirred for 16 h. HPLC revealed no detectable starting material, so H₂O (50 mL) was added. The inorganic salt promptly dissolved, followed immediately by crystallization of the product. Following filtration, an H₂O wash (50 mL) of the cake, and drying in vacuo at 50° C., provided the final title compound as a light tan crystalline solid (3.07 g, 90.0%) in outstanding purity: mp 68.5–69.5° C. Clean ¹H and ¹³C NMR (CDCl₃) spectra. Satisfactory elemental analysis was obtained when block dried at 60° C. Purity of 99.6% by HPLC.

Preparation 2

Preparation of 2-Bromo-7-methoxy-naphthalene.

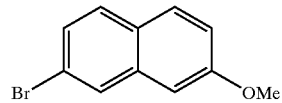

Preparation of 7-Bromo-2-naphthalenol.

Triphenyl phosphine (89.7 g, 0.342 mol) and acetonitrile (350 mL) were combined in a 1-L flask under N₂ atmosphere. The mixture was cooled to 10° C. Bromine (17.6 mL, 0.342 mol) was added dropwise over 10 minutes. The cooling bath was removed and 2,7-dihydroxynaphthalene (50.0 g, 0.312 mol) was added along with 350 mL of CH₃CN rinse. The resulting yellow tan mixture was heated at reflux for 3 hours. Acetonitrile was distilled off using a water aspirator over 2 hours resulting in a grayish white solid. The solid was heated to 280° C. over 30 minutes giving a black liquid. The liquid was heated to 310° C. over 20 minutes and the temperature was maintained at 310° C. for an additional 15 minutes until gas evolution ceased. The black mixture was cooled to room temperature. Chromatography yielded 34.5 g of the intermediate title compound as an off-white solid which was 87% pure by HPLC (43% yield).

Preparation of the Final Title Compound.

2-Bromo-7-hydroxynaphthalene (34.1 g, 0.134 mol), DMF (290 mL) and powdered potassium carbonate (31.8 g, 0.230 mol) were combined in a 500-mL flask under N₂ atmosphere. Methyl iodide (14.3 mL, 0.230 mol) was added at once and the dark yellow mixture was stirred vigorously at room temperature for 3¾ hours. Water (290 mL) was added dropwise over 15 minutes to induce crystallization. The mixture was stirred at room temperature for 1 hour. The product was filtered off and washed with 200 mL of a 1:1 mixture of DMF and water. The solid was dried in vacuo at 50° C. to yield 32.6 g of pale yellow solid (HPLC: 89%). The solid was dissolved in 300 mL of boiling MeOH. The hot solution was filtered, then placed in the freezer overnight. The resulting crystals were filtered and washed with 100 mL of cold MeOH. The solid was dried in vacuo at 50° C. to give 27.0 g of pale yellow solid (HPLC: 95%). The solid was dissolved in 100 mL of boiling i-PrOH then allowed to cool to room temperature. The resulting solid was filtered and washed with 100 mL of i-PrOH. The solid was dried in vacuo at 50° C. to yield 22.8 g of the title compound as pale yellow crystals.

Preparation 3
Preparation of 6-Iodo-1-methoxy-naphthalene.

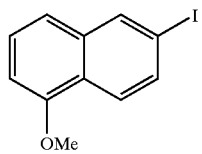

Preparation of 5-Bromo-2-naphthalenecarboxylic Acid.

2-Naphthoic acid (50.0 g, 0.290 mol), glacial acetic acid (250 mL), bromine (15 mL, 0.291 mol) and iodine (1.3 g, 0.005 mol) were combined in a flask under $N_2$ atmosphere. The mixture was heated at reflux for 35 minutes then cooled to room temperature. The thick yellow mixture was stirred at room temperature for 1 hour. The mixture was filtered and the pale orange solid was rinsed with ~100 mL of the filtrate. The solid was dried in vacuo at 55° C. overnight to yield 55.5 g of pale orange solid. The solid was slurried in 275 mL of 1 N NaOH for 30 minutes. The solid was filtered off and rinsed 3 times with 50 mL portions of the filtrate. The solid was air dried in the hood over the weekend to yield 46.7 g of solid. The solid was added to 220 mL of water. Concentrated HCl (15 mL) was added to obtain pH of 1.3 and the mixture was stirred for 4 hours. The solid was filtered off and washed with 200 mL of water. The solid was dried in vacuo at 50° C. to give 37.6 g of intermediate title compound as white crystals (HPLC: 90% with 9% 2-naphthoic acid, 46% yield).

Preparation of 5-Bromo-2-naphthalenecarboxylic Acid, Methyl Ester.

5-Bromo-2-naphthoic acid (17.33 g, 69 mmol) and 250 mL of MeOH were combined in a flask under $N_2$ atmosphere. Thionyl chloride (5.84 mL, 80 mmol) was added dropwise over 15 minutes at a temperature of 25–30° C. resulting in a pale yellow mixture. The mixture was heated at reflux for 3¼ hours. The resulting yellow solution was concentrated in vacuo to 137.4 g of solution then placed in the freezer overnight. The resulting thick mixture was filtered and the solid was washed with 100 mL of cold MeOH. The solid was dried in vacuo at 50° C. to give 11.39 g of intermediate title compound as white crystals. A second crop was filtered and washed with 100 mL of cold MeOH. The solid was dried to 1.31 g of white crystals. Yield: 69%, 2 crops.

Preparation of 5-Methoxy-2-naphthoic Acid.

A 25% solution of sodium methoxide in MeOH (63 mL, 0.258 mol) was added to a 500-mL flask under $N_2$ atmosphere. Cupric iodide (recrystallized, 4.19 g, 22 mmol), 160 mL of pyridine, 160 mL of MeOH and methyl 5-bromo-2-naphthoate (11.39 g, 43 mmol) were added to the flask to give a yellow green mixture. The mixture was heated at reflux for 30 hours. The mixture was cooled to room temperature and water (850 mL) was added resulting in a rust colored mixture having pH of 12.8. The pH was adjusted to 1.0 by addition of concentrated HCl resulting in a white precipitate. The mixture was cooled to 10° C., filtered and the solid was washed with cold water. The solid was dried to 11.03 g white crystals. The solid was taken up in 200 mL of EtOAc and 150 mL of water. The pH of the mixture was 3.5. The pH was adjusted to 10.0 by addition of 5 N NaOH and maintained for 4 hours. The EtOAc was removed by concentration in vacuo then the pH was adjusted to 1.0 by addition of concentrated HCl. The mixture was placed in a freezer overnight. The mixture was filtered and the solid was washed with water until the filtrate stream was colorless. The solid was dried in vacuo at 50° C. to give 9.77 g of off-white solid. The solid was added to 50 mL of 2.5 N NaOH and the thick orange mixture was stirred for 3 hours. The pH was adjusted to 1.0 with concentrated HCl. The mixture was filtered and the solid was washed with water. The solid was dried to 9.43 g of off-white solid. The solid was dissolved in 200 mL of boiling MeOH and the hot solution was filtered then cooled to room temperature. Water (300 mL) was added and the mixture was stirred at room temperature for 2 hours. The solid was filtered off and washed with 100 mL of a 1:1 mixture of MeOH and water. The solid was dried in vacuo at 50° C. to give 7.18 g of intermediate title compound as a white solid (HPLC: 97%, 83% yield).

Preparation of 5-Methoxy-2-Naphthylamine.

5-Methoxy-2-naphthoic acid (3.17 g, 15.7 mmol), $CH_2CO_2$ (38 mL) and DMF (3.04 mL, 39.2 mmol) were combined in a 50-mL flask under a $N_2$ atmosphere. Oxalyl chloride (2.73 mL, 31.3 mmol) was added dropwise over 30 minutes at 20 to 23° C. The resulting yellow solution was stirred at room temperature for 15 minutes. The solution was then concentrated in vacuo to 6.48 g of yellow solid which was slightly wet with DMF. The solid was dissolved in $CH_3CN$ (157 mL) and added dropwise over 35 minutes to a solution of sodium azide (2.55 g, 39.2 mmol) in 24 mL of water, and rinsed in with an additional 25 mL of $CH_3CN$. Analysis of the resulting yellow mixture by HPLC after 5 minutes showed 15% acyl chloride remaining. Water (15 mL) was added to give an orange mixture and to promote acyl azide formation. The mixture was heated at reflux for 1 hour and 40 minutes. The mixture was cooled to room temperature. Sodium hydroxide (50 mL, 2N solution) was added and the resulting yellow mixture was stirred at room temperature overnight. The mixture was concentrated in vacuo to 102.0 g of brown gum plus liquid. The mixture was extracted with 50 mL of $CH_2Cl_2$. The $CH_2Cl_2$ layer was dried over $Na_2SO_4$, filtered and concentrated in vacuo to provide 1.83 g of the intermediate title compound as a brown oil (HPLC: 91%, 61% yield).

Preparation of the Final Title Compound.

2-Amino-5-methoxynaphthalene (1.78 g, 9.35 mmol), 5 mL of concentrated HCl(aq), 5 mL of water and 10 g of ice were combined in a flask. The tan orange mixture was cooled to 5° C. A chilled solution of sodium nitrite (0.75 g, 10.8 mmol) in 4 mL of water was added over 5 minutes keeping the temperature below 10° C. The mixture was stirred at 5° C. for 30 minutes. A solution of potassium iodide (1.71 g, 10.3 mmol) in 10.5 mL of water was added, the bath was removed and the orange solution plus black solid was stirred at room temperature. Analysis by HPLC showed that more KI was needed. Potassium iodide (7.2 g, 43.4 mmol), 100 mL of $CH_3CN$ and 50 mL of acetone were added and the mixture was stirred for 22 hours at room temperature. The mixture was extracted with 150 mL of $Et_2O$. The $Et_2O$ phase was washed successively with 200 mL of 5% $NaHSO_{3(aq)}$, 200 mL of 5% $NaHCO_{3(aq)}$, 200 mL of water and 200 mL of saturated NaCl solution. The $Et_2O$ phase was dried over $Na_2SO_4$, filtered and concentrated in vacuo to yield 2.21 g of dark brown solid (HPLC: 69.5%). The solid was adsorbed onto 8.0 g of silica gel 60 in $CH_2Cl_2$ then concentrated to a powder. The powder was slurried in hexane and chromatographed on 100 g of silica gel 60 at atmospheric pressure, eluting with hexane. The desired final title compound was collected (1.33 g, 50% yield) as a white solid after concentration of the appropriate fractions.

Preparation 4
Preparation of N-(t-Butyloxycarbonyl)-2-methyl-4-piperidone.

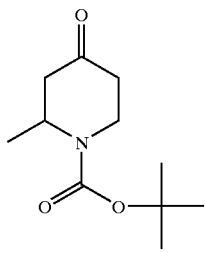

A solution of the following protected amine;

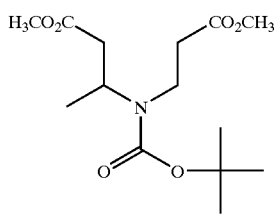

(145 g, prepared in a manner analogous to the procedures described by Hall, H. K. Jr., *J. Am. Chem. Soc.*, 79, 5444 (1957) and Harper, N. J.; Beckett, A. H.; Balon, A. D. J., *J. Chem. Soc.*, 2704 (1960)) dissolved in THF (200 mL) was added dropwise over one hour to a cooled solution of potassium t-butoxide (58.9 g) in THF (500 mL). The mixture was stirred at 0° C. for 2.5 hours and then warmed to room temperature over 1 hours with stirring. Another 50 mL of 1.0 M potassium t-butoxide in THF was added. After one hour, the solvent was removed under vacuum and the residue was dissolved in ethyl acetate (1 L). The organic solution was washed with saturated ammonium chloride (2×500 mL) which was back extracted with ethyl acetate (2×500 mL). The organic extracts were combined, dried over anhydrous magnesium sulfate, filtered and concentrated under vacuum to provide 120. 6 g of crude material as an oil. This oil was then treated with 5 N HCl (700 mL) at reflux for about 14.5 hours. After cooling, the solution was rinsed with a mixture of ethyl acetate/diethyl ether (1:1, 2×300 mL). The aqueous layer was then concentrated to provide the piperidone salt of structure:

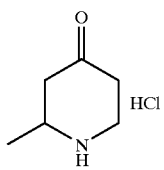

The above piperidone salt was then dissolved in water (200 mL) and THF (250 mL). The solution was then cooled to 0° C. and treated with 50% sodium hydroxide (35 mL) followed by dropwise addition of tert-butoxycarbonyl anhydride (106.7 g) in THF (100 mL) over one hour. The ice bath was then removed and the solution was stirred at room temperature for about 4 days. The pH was then adjusted to about 8 to 9. The THF was then removed under vacuum and the mixture is taken up in ethyl acetate (500 mL). The layers were separated and the aqueous layer was extracted with ethyl acetate (2×500 mL). The organic extracts were combined, washed with brine (300 mL), dried over anhydrous magnesium sulfate, filtered and concentrated under vacuum. The residue was purified by chromatography on silica gel (ethyl acetate/hexanes) to provide 36.81 g of title compound.

Preparation 5
Preparation of N-(t-Butyloxycarbonyl)-2,2-dimethyl-4-piperidone

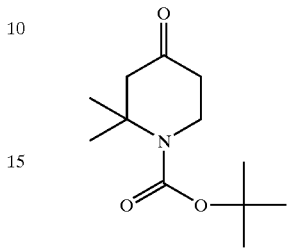

In a manner analogous to the procedure described in preparation 4 above, the title compound can be prepared from the following starting material;

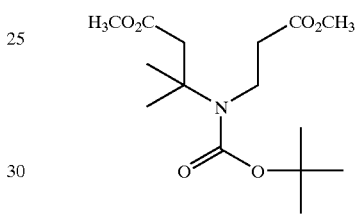

Preparation 6
Preparation of N-Benzyl-3,3-dimethyl-4-piperidone.

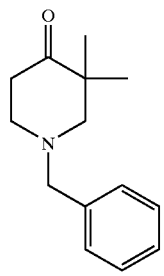

In a 1 liter 3-neck flask equipped with a mechanical stirrer, an addition funnel and a calcium chloride drying tube was added a 37% weight solution of formaldehyde (168.5 mL, 2.25 mole) dissolved in 500 mL of absolute ethanol. The resulting solution was cooled in an ice-water bath to 10° C., and benzylamine (109 mL, 1 mole) was added dropwise over a one hour period. In a separate 3-liter 3-neck flask equipped with a mechanical stirrer, an addition funnel and two condensers was added 3-methyl-2-butanone (113 mL, 1.06 mole) dissolved in 500 ml of absolute ethanol and concentrated hydrogen chloride (92 mL, 1.11 mole). The resulting solution was brought to reflux and the formaldehyde/benzylamine solution is added dropwise over a 2 hour period. This solution was heated at reflux overnight, and then cooled to ambient temperature. Diisopropylethylamine (142.2 g, 1.1 mole) and formaldehyde (22.46 mL, 0.3 mole) were added and the resulting solution was heated to reflux for six hours, and then cooled to ambient temperature. The solution was quenched with potassium hydroxide (61.6 g, 1.1 mole) in 200 mL of water, and then extracted 3 times with 500 ml ethyl acetate. The organic layers were concentrated under vacuum to give 225 g of a red oil. The crude oil was dissolved in 1 liter of methylene chloride. This solution was carefully poured over 1 kg of silica gel on a sintered glass filter. The silica gel was washed with 4 L of methylene chloride. The methylene chloride was concentrated under vacuum to provide 142 g of a yellow oil which was crystallized in a freezer overnight. Yield=65.4%. MS(ion spray)=218.3 (M+1)

EXAMPLE 1

Preparation of (2S)-(−)-1-(4-Benzo[b]thiophenoxy)-3-(4-(3-methylbenzo[b]thiophen-2-yl)piperidin-1-yl)-2-propanol Oxalate.

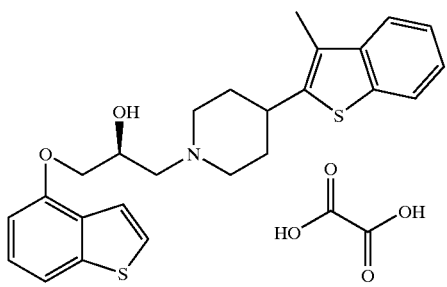

Preparation of 4-Hydroxy-4-(3-Methylbenzo[b]thiophen-2-yl)-1-(2-Propenyl)-piperidine.

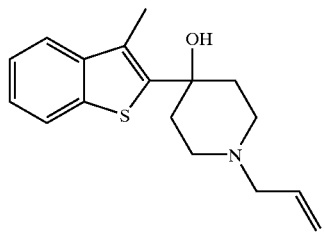

Scheme IA, step A: To a solution of 3-methylbenzothiophene (2.863 g, 19.3 mmol) in tetrahydrofuran (80 mL) at −78° C. was added a solution of n-butyllithium (13.3 mL, 21.2 mmol, 1.6 M in hexanes). The solution was warmed to 0° C. for one hour then recooled to −78° C. A solution of 1-(2-propenyl)-4-piperidone (2.957 g, 21.2 mmol) in tetrahydrofuran was added dropwise and the mixture was warmed to 20° C. After stirring for 18 hours at 20° C. the mixture was diluted with brine and extracted 3 times with ethyl acetate. The combined organics were dried over sodium sulfate then filtered and evaporated. The residue was purified using silica gel chromatography (dichloromethane/5% methanol in dichloromethane gradient eluent) to give 4.61 g (83%) of the intermediate title compound as a white amorphous solid. FDMS m/e=288 (M⁺+1).

Preparation of 4-Hydroxy-4-(3-methylbenzo[b]thiophen-2-yl)piperidine.

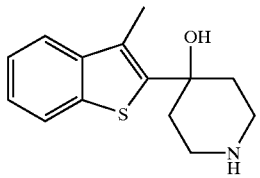

Scheme IC: To a solution of 4-hydroxy-4-(3-methylbenzo[b]thiophen-2-yl)-1-(2-propenyl)piperidine (2.821 g, 9.81 mmol) in aqueous ethanol (65 mL, 10% $H_2O$) was added chlorotris(triphenylphosphine) rhodium(I) (Wilkinson's catalyst) (45 mg, 0.0486 mmol). Approximately 50% of the solvent was distilled off over a period of 1 hour. An additional 65 mL of solvent and 45 mg of Wilkinson's catalyst was added. The mixture was refluxed for 1 hour and then the solvent was distilled off to about 50% volume. The mixture was heated at reflux and the residue was purified using silica gel chromatography (dichloromethane/20% methanol, 2% anhydrous ammonia in dichloromethane gradient eluent) to give 1.55 g (64%) of the intermediate title compound as an amorphous white powder. FDMS m/e=248 ($M^+$+1).

Preparation of the Final Title Compound.

Scheme IV, Step B: A solution 4-hydroxy-4-(3-methylbenzo[b]thiophen-2-yl)piperidine (0.078 g, 0.337 mmol) and (S)-(+)-4-(oxiranylmethoxy)benzo[b]-thiophene (0.070 g, 0.337 mmol) in methanol (3 mL) was heated at reflux for 18 hours and then cooled and evaporated. The residue was purified using silica gel chromatography (dichloromethane/2% methanol in dichloromethane gradient elution) to give the free base of the title compound as a clear colorless oil (0.081 g, 55%). The oxalate salt was prepared to give the title compound. FDMS m/e=438 ($M^+$+1 of free base). $[\alpha]_D = -1.99$ (c=0.502, methanol). $C_{25}H_{27}NO_2S_2 \cdot C_2H_2O_4$

| analysis: | Calculated | found |
| --- | --- | --- |
| C | 61.46 | 61.73 |
| H | 5.54 | 5.48 |
| N | 2.65 | 2.67 |

EXAMPLE 2

Preparation of (2S)-(−)-1-(4-Benzo[b]thiophenoxy)-3-(4-(3-ethylbenzo[b]thiophen-2-yl)piperidin-1-yl)-2-propanol Oxalate.

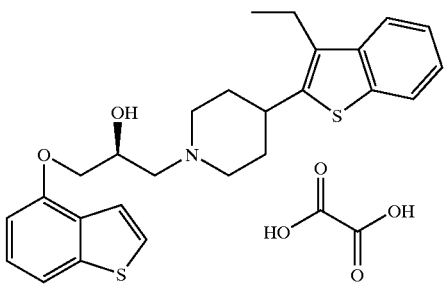

Preparation of 3-(1-Hydroxyethyl)benzo[b]thiophene.

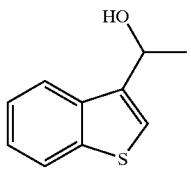

To a solution of 3-acetyl thianaphthene (2.024 g, 11.5 mmol) in ethanol (15 mL) was added sodium borohydride (0.434 g, 11.5 mmol). The mixture was stirred at 20° C. for 4 hours then evaporated, diluted with brine and extracted 3 times with ethyl acetate. The combined organics were dried over sodium sulfate, filtered and evaporated to give the intermediate title compound as a clear oil (1.924 g, 94%) which was used as is in subsequent reactions. FDMS m/e= 178 (M$^+$).

Preparation of 4-Hydroxy-4-(3-(1-hydroxyethyl)benzo[b]thiophen-2-yl)-1-(t-butyloxycarbonyl)piperidine.

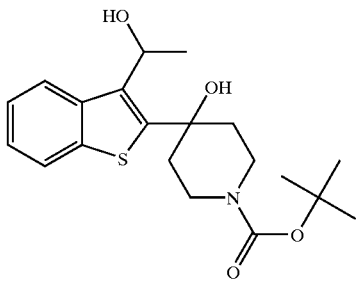

Scheme IA, Step A: To a solution of 3-(1-hydroxyethyl)benzo[b]thiophene (2.036 g, 11.4 mmol) in tetrahydrofuran (75 mL) at −78° C. was added a solution of n-butyllithium (15.7 mL, 25.1 mmol, 1.6 M in hexanes). The solution was warmed to 0° C. for one hour then recooled to −78° C. A solution of 1-t-butyloxycarbonyl-4-piperidone (2.503 g, 12.6 mmol) in tetrahydrofuran was added dropwise and the mixture was warmed to 20° C. After stirring for 6 hours at 20° C. the mixture was diluted with brine and extracted 3 times with ethyl acetate. The combined organics were dried over sodium sulfate then filtered and evaporated. The residue was purified using silica gel chromatography (dichloromethane/5% methanol in dichloromethane gradient eluent) to give 3.75 g (87%) of the intermediate title compound as a yellow amorphous solid. FDMS m/e=378 (M$^+$+1).

Preparation of 4-(3-Ethylbenzo[b]thiophen-2-yl)-1,2,5,6-tetrahydropyridine.

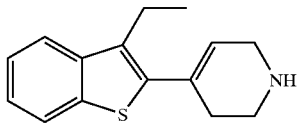

Scheme IA, Step B: 4-Hydroxy-4-(3-(1-hydroxyethyl)benzo[b]thiophen-2-yl)-1-(t-butyloxycarbonyl)piperidine (1.038 g, 2.75 mmol) was slowly added in portions to trifluoroacetic acid (6 mL). To this mixture was added triethylsilane (1.0 mL, 6.05 mmol) dropwise. The solution was stirred at 20° C. for 3 hours then diluted with 2 N sodium hydroxide and extracted 3 times with ethyl acetate. The combined organics were dried over sodium sulfate, filtered and evaporated. The residue was chromatographed (dichloromethane/20% methanol, 2% anhydrous ammonia in dichloromethane gradient eluent) to give the intermediate title compound as a yellow solid (0.484 g, 72%). FDMS m/e=244 (M$^+$+1).

Preparation of 4-(3-Ethylbenzo[b]thien-2-yl)piperidine.

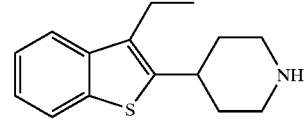

Scheme IA, Step C: To a mixture of 4-(3-ethylbenzo[b]thiophen-2-yl)-1,2,5,6-tetrahydropyridine (0.465 g, 1.91 mmol) in ethanol (15 mL) and 2,2,2-trifluoroethanol (5 mL) was added 10% palladium on carbon (0.25 g). The mixture was hydrogenated at one atmosphere for 24 hours. The mixture was carefully filtered and evaporated to give the intermediate title compound as a yellow amorphous solid (0.395 g, 84%). FDMS m/e=246 (M$^+$+1).

Preparation of the Final Title Compound.

Scheme IV, Step B: A solution 4-hydroxy-4-(3-ethylbenzo[b]thiophen-2-yl)piperidine (0.069 g, 0.281 mmol) and (S)-(+)-4-(oxiranylmethoxy)-benzo[b]thiophene (0.058 g, 0.281 mmol) in methanol (3 mL) was heated at reflux for 18 hours and then cooled and evaporated. The residue was purified using silica gel chromatography (dichloromethane/1% methanol in dichloromethane) to give the free base of the final title compound as a clear colorless oil (0.050 g, 39%). The oxalate salt was prepared to give the title compound. FDMS m/e=452 (M$^+$+1 of free base). $C_{26}H_{29}NO_2S_2 \cdot C_2H_2O_4$

| analysis: | Calculated | found |
|---|---|---|
| C | 62.09 | 62.29 |
| H | 5.77 | 5.52 |
| N | 2.59 | 2.58 |

EXAMPLE 3

Preparation of (2S)-(−)-1-(4-Benzo[b]thiophenoxy)-3-(4-(6-fluoronaphth-2-yl)-1,2,5,6-tetrahydropyrid-1-yl)-2-propanol oxalate.

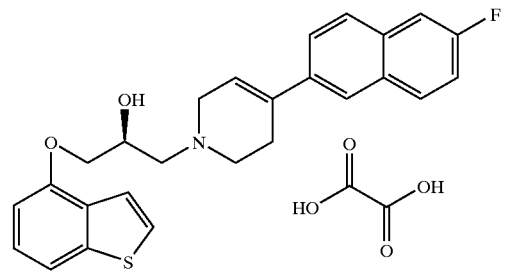

Scheme IV, Step B: A solution 4-(6-fluoronaphth-2-yl)-1,2,5,6-tetrahydropyridine (0.094 g, 0.414 mmol) and (S)-(+)-4-(oxiranylmethoxy)-benzo[b]thiophene (0.085 g, 0.414 mmol) in methanol (4 mL) was refluxed for 18 hours and then cooled and evaporated. The residue was purified using silica gel chromatography (dichloromethane/2% methanol in dichloromethane gradient elution) to give the free base of the title compound as a yellow oil (0.130 g, 73%). The oxalate salt was prepared to give the title compound. FDMS m/e=434 (M⁺+1 of free base). [α]$_D$=−7.75 (c=0.516, methanol). $C_{26}H_{24}FNO_2S \cdot C_2H_2O_4$

| analysis: | Calculated | found |
|---|---|---|
| C | 64.23 | 63.83 |
| H | 5.01 | 4.92 |
| N | 2.68 | 2.30 |

EXAMPLE 4
Preparation of (2S)-(−)-1-(4-Benzo[b]thiophenoxy)-3-(4-(6-fluoronaphth-2-yl)Piperidin-1-yl)-2-propanol.

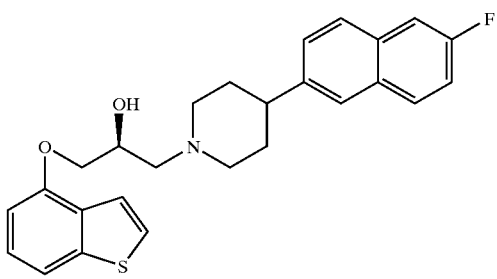

Scheme IV, Step B: A solution 4-(6-fluoronaphth-2-yl) piperidine (0.069 g, 0.301 mmol) and (S)-(+)-4-(oxiranylmethoxy)benzo[b]thiophene (0.062 g, 0.301 mmol) in methanol (3 mL) was heated at reflux for 18 hours and then cooled and evaporated. The residue was purified using silica gel chromatography (dichloromethane/5% methanol in dichloromethane gradient elution) to give the title compound as a white amorphous solid (0.066 g, 50%). FDMS m/e 436 (M⁺+1). $C_{26}H_{26}FNO_2S$.

| analysis: | Calculated | found |
|---|---|---|
| C | 71.70 | 71.77 |
| H | 6.02 | 5.83 |
| N | 3.22 | 3.16 |

Serotonin $1_A$ Receptor Activity

The compounds of the present invention are active at the serotonin $1_A$ receptor, particularly as antagonists and as partial agonists at that receptor, and are distinguished by their selectivity. It is now well understood by pharmacologists and physicians that pharmaceuticals which have a single physiological activity, or which are much more active in the desired activity than in their other activities, are much more desirable for therapy than are compounds which have multiple activities at about the same dose.

The 5-HT$_{1A}$ receptor binding potency of the present compounds are measured by a modification of the binding assay described by Taylor, et al. (J. Pharmacol. Exp. Ther. 236, 118–125, 1986); and Wong, et al., Pharm. Biochem. Behav. 46, 173-77 (1993). Membranes for the binding assay are prepared from male Sprague-Dawley rats (150–250 g). The animals are killed by decapitation, and the brains are rapidly chilled and dissected to obtain the hippocampi. Membranes from the hippocampi are either prepared that day, or the hippocampi are stored frozen (−70° C.) until the day of preparation. The membranes are prepared by homogenizing the tissue in 40 volumes of ice-cold Tris-HCl buffer (50 mM, pH 7.4 at 22° C.) using a homogenizer for 15 sec., and the homogenate is centrifuged at 39800xg for 10 min. The resulting pellet is then resuspended in the same buffer, and the centrifugation and resuspension process is repeated three additional times to wash the membranes. Between the second and third washes the resuspended membranes are incubated for 10 min. at 37° C. to facilitate the removal of endogenous ligands. The final pellet is resuspended in 67 mM Tris-HCl, pH 7.4, to a concentration of 2 mg of tissue original wet weight/200 μL. This homogenate is stored frozen (−70° C.) until the day of the binding assay. Each tube for the binding assay has a final volume of 800 μL and contains the following: Tris-HCl (50 mM), pargyline (10 μM), CaCl$_2$ (3 mM), [³H]8-OH-DPAT (1.0 nM), appropriate dilutions of the drugs of interest, and membrane resuspension equivalent to 2 mg of original tissue wet weight, for a final pH of 7.4. The assay tubes are incubated for either 10 min. or 15 min. at 37° C., and the contents are then rapidly filtered through GF/B filters (pretreated with 0.5% polyethylenimine), followed by four one-mL washes with ice-cold buffer. The radioactivity trapped by the filters is quantitated by liquid scintillation spectrometry, and specific [³H]8-OH-DPAT binding to the 5-HT$_{1A}$ sites is defined as the difference between [³H]8-OH-DPAT bound in the presence and absence of 10 μM 5-HT.

IC$_{50}$ values, i.e., the concentration required to inhibit 50% of the binding, are determined from 12-point competition curves using nonlinear regression (SYSTAT, Inc., Evanston, Ill.). IC$_{50}$ values are converted to K$_i$ values using the Cheng-Prusoff equation (Biochem. Pharmacol., 22, 3099–3108 (1973)).

Additional binding assays of some of the present compounds are carried out by an assay method which uses a cloned cell line which expresses the serotonin 1A receptor, rather than the hippocampal membranes. Such cloned cell lines have been described by Fargin, et al., J. Bio. Chem., 264,14848–14852 (1989), Aune, et al., J. Immunology, 151, 1175–1183 (1993), and Raymond, et al., Naunyn-Schmiedeberg's Arch. Pharmacol., 346, 127–137 (1992). Results from the cell line assay are substantially in agreement with results from the hippocampal membrane assay.

As was reported by R. L. Weinshank, et al., WO93/14201, the 5-HT$_{1A}$ receptor is functionally coupled to a G-protein as measured by the ability of serotonin and serotonergic drugs to inhibit forskolin stimulated cAMP production in NIH3T3 cells transfected with the 5-HT$_{1A}$ receptor. Adenylate cyclase activity is determined using standard techniques. A maximal effect is achieved by serotonin. An Emax is determined by dividing the inhibition of a test compound by the maximal effect and determining a percent inhibition. (N. Adham, et al., supra,; R. L. Weinshank, et al., Proceedings of the National Academy of Sciences (USA), 89,3630–3634 (1992)), and the references cited therein.

Measurement of cAMP Formation

Transfected NIH3T3 cells (estimated Bmax from one point competition studies=488 fmol/mg of protein) are incubated in DMEM, 5 mM theophylline, 10 mM HEPES (4-[2-hydroxyethyl]-1-piperazineethanesulfonic acid) and 10 μM pargyline for 20 minutes at 37° C., 5% carbon dioxide. Drug dose-effect curves are then conducted by adding 6 different final concentrations of drug, followed immediately by the addition of forskolin (10 mM). Subsequently, the cells are incubated for an additional 10 minutes at 37° C., 5% carbon dioxide. The medium is aspirated and the reaction is stopped by the addition of 100 mM hydrochloric acid. To demonstrate competitive antagonism, a dose-response curve for 5-HT is measured in parallel, using a fixed dose of methiothepin (0.32 mM). The plates are stored at 4° C. for 15 minutes and then centrifuged for 5 minutes at 500×g to pellet cellular debris, and the supernatant is aliquoted and stored at −20° C. before assessment of cAMP formation by radioimmunoassay (cAMP radioimmunoassay kit; Advanced Magnetics, Cambridge, Mass.). Radioactivity is quantified using a Packard COBRA Auto Gamma counter, equipped with data reduction software. Representative compounds are tested for 5-HT$_{1A}$ receptor antagonist activity in the cAMP assay.

5HT$_{1A}$ Antagonist, in Vivo Tests a) 5HT$_{1A}$ Antagonism Subcutaneous Test

Compounds are tested over a range of subcutaneous doses for activity in blocking the 8-OH-DPAT induced behaviors and hypothermia. Lower lip retraction (LLR) and flat body posture (FBP) are recorded in male Sprague Dawley rats (~250 grams from Harlan Sprague Dawley). Both LLR and FBP are measured on a scale of 0–3 (Wolff et al, 1997). In the LLR behavioral assay, "0" indicates normal lip position; "1" indicates a slight separation of the lips; "2" indicates that the lips are open with some teeth visible; "3" indicates that the lips are fully open with all the front teeth exposed. In the FBP assay, a score of "0" indicates normal body posture; "1" indicates that the stomach is on the floor with the back in its normal rounded position; "2" indicates that the stomach is on the floor with the back straightened and rising from the shoulders to the hips; "3" indicates that the stomach is pressed into the floor and the back is flattened with the shoulders and hips even. Core body temperature is recorded by rectal probe inserted 5.0 cm immediately after the behavioral measures. Rats are injected subcutaneous with compound (at 0, 0.3, 1.0 and 3.0 mg/kg) 35 minutes before scoring and the 8-OH-DPAT (0.1 mg/kg subcutaneous) is injected 20 minutes before scoring.

b) 5HT$_{1}$A Agonist Subcutaneous Test

The compounds are also tested at a high dose of 10 mg/kg subcutaneous alone to see if they induced 5HT$_{1A}$ agonist-like hypothermia.

The efficacy of the compounds of the invention to inhibit the reuptake of serotonin is determined by a paroxetine binding assay, the usefulness of which is set out by Wong, et al., *Neuropsychopharmacology*, 8, 23–33 (1993). Synaptosomal preparations from rat cerebral cortex are made from the brains of 100–150 g Sprague-Dawley rats which are killed by decapitation. The cerebral cortex is homogenized in 9 volumes of a medium containing 0.32 M sucrose and 20 $\mu$M glucose. The preparations are resuspended after centrifugation by homogenizing in 50 volumes of cold reaction medium (50 $\mu$M sodium chloride, 50 $\mu$M potassium chloride, pH 7.4) and centrifuging at 50,000 g for 10 minutes. The process is repeated two times with a 10-minute incubation at 37° C. between the second and third washes. The resulting pellet is stored at −70° C. until use. Binding of $^3$H-paroxetine to 5-HT uptake sites is carried out in 2 mL reaction medium containing the appropriate drug concentration, 0.1 nM $^3$H-paroxetine, and the cerebral cortical membrane (50 $\mu$g protein/tube). Samples are incubated at 37° C. for 30 minutes; those containing 1 $\mu$M fluoxetine are used to determine nonspecific binding of $^3$H-paroxetine. After incubation, the tubes are filtered through Whatman GF/B filters, which are soaked in 0.05% polyethylenimine for 1 hour before use, using a cell harvester by adding about 4 mL cold Tris buffer (pH 7.4), aspirating, and rinsing the tubes three additional times. Filters are then placed in scintillation vials containing 10 mL scintillation fluid, and the radioactivity is measured by liquid scintillation spectrophotometry.

The pharmacological activities which have been described immediately above provide the mechanistic basis for the pharmaceutical utility of the compounds described in this document. A number of pharmaceutical utilities will be described below.

The activity of the compounds at the serotonin 1$_A$ receptor provides a method of affecting the serotonin 1$_A$ receptor which comprises administering to a patient in need of such treatment an effective amount of a compound of formula I. Reasons for the necessity of affecting the serotonin 1$_A$ receptor will be described in detail below, but in all cases the effect on the serotonin $_1$A receptor is brought about through the compounds' potency as antagonists or partial agonists at that receptor. A patient in need of a modification of the effects of the 5-HT$_{1A}$ receptor is one having one or more of the specific conditions and problems to be further described, or a condition or problem not yet recognized as created by an imbalance or malfunction of the 5-HT$_{1A}$ receptor, since research on the central nervous system is presently ongoing in many fields and newly discovered relationships between receptors and therapeutic needs are continually being discovered. In all cases, however, it is the compounds' ability to affect the serotonin 1$_A$ receptor which creates their physiological or therapeutic effects.

Further, the activity of compounds of formula I in the inhibition of the reuptake of serotonin provides a method of inhibiting the reuptake of serotonin comprising administering to a patient in need of such treatment an effective amount of a compound of that formula. The treatment of depression with drugs of the class of which fluoxetine is the leader has become perhaps the greatest medical breakthrough of the past decade. Numerous other treatment methods carried out by the administration of the compounds of formula I will be set out in detail below.

The unique combination of 5-HT$_{1A}$ receptor activity and serotonin reuptake inhibition possessed by the compounds of the invention afford a method of providing to a patient both physiological activities with a single administration of a compound of that formula. As discussed in the Background section of this document, the value of combining the two effects has been discussed in the literature, and it is believed that the present compounds are advantageous in that they provide both physiological effects in a single drug. It is presently believed that the result of administration of a compound of formula I is to provide physiological and therapeutic treatment methods which are typical of those provided by presently known serotonin reuptake inhibitors, but with enhanced efficacy and quicker onset of action.

The activities of compounds of formula I at the 5-HT$_{1A}$ receptor and in reuptake inhibition are of comparable potencies, so an effective amount as defined hereinabove for affecting the serotonin 1$_A$ receptor or for inhibiting the reuptake of serotonin, is effective for affecting the serotonin 1$_A$ receptor and for inhibiting the reuptake of serotonin in a patient.

Further discussion of specific therapeutic methods provided by the dual activity compounds of formula I, and the diseases and conditions advantageously treated therewith, are provided below.

The compounds of the present invention are useful for binding, blocking or modulating the serotonin receptor, and for the treatment of conditions caused by or influenced by defective function of that receptor. In particular, the compounds are useful for antagonism at the serotonin 1$_A$ receptor, and accordingly, are useful for the treatment of conditions caused by or affected by excessive activity of that receptor.

More particularly, the compounds are useful in the treatment of anxiety, depression, hypertension, cognitive disorders, Alzheimer's disease, psychosis, sleep disorders, gastric motility disorders, sexual dysfunction, brain trauma, memory loss, appetite disorders, bulimia, obesity, substance abuse, obsessive-compulsive disease, panic disorder and migraine.

Depression in its many variations has recently become much more visible to the general public than it has previously been. It is now recognized as an extremely damaging disorder, and one that afflicts a surprisingly large fraction of the human population. Suicide is the most extreme symptom of depression, but millions of people, not quite so drastically afflicted, live in misery and partial or complete uselessness, and afflict their families as well by their affliction. The introduction of fluoxetine was a breakthrough in the treatment of depression, and depressives are now much more likely to be diagnosed and treated than they were only a decade ago.

Depression is often associated with other diseases and conditions, or caused by such other conditions. For example, it is associated with Parkinson's disease; with HIV; with Alzheimer's disease; and with abuse of anabolic steroids. Depression may also be associated with abuse of any substance, or may be associated with behavioral problems resulting from or occurring in combination with head injuries, mental retardation or stroke. Depression in all its variations is a preferred target of treatment with the compounds of the present invention.

Obsessive-compulsive disease appears in a great variety of degrees and symptoms, generally linked by the victim's uncontrollable urge to perform needless, ritualistic acts. Acts of acquiring, ordering, cleansing and the like, beyond any rational need or rationale, are the outward characteristic of the disease. A badly afflicted patient may be unable to do anything but carry out the rituals required by the disease. Fluoxetine is approved in the United States and other countries for the treatment of obsessive-compulsive disease and has been found to be effective.

Obesity is a frequent condition in the American population. It has been found that fluoxetine will enable an obese patient to lose weight, with the resulting benefit to the circulation and heart condition, as well as general well being and energy.

Urinary incontinence is classified generally as stress or urge incontinence, depending on whether its root cause is the inability of the sphincter muscles to keep control, or the overactivity of the bladder muscles.

The present treatment methods are useful for treating many other diseases, disorders and conditions as well, as set out below. In many cases, the diseases to be mentioned here are classified in the International Classification of Diseases, 9th Edition (ICD), or in the Diagnostic and Statistical Manual of Mental Disorders, 3rd Version Revised, published by the American Psychiatric Association (DSM). In such cases, the ICD or DSM code numbers are supplied below for the convenience of the reader.

depression, ICD 296.2 & 296.3, DSM 296, 294.80, 293.81, 293.82, 293.83, 310.10, 318.00, 317.00
migraine
pain, particularly neuropathic pain
bulimia, ICD 307.51, DSM 307.51
premenstrual syndrome or late luteal phase syndrome, DSM 307.90
alcoholism, ICD 305.0, DSM 305.00 & 303.90
tobacco abuse, ICD 305.1, DSM 305.10 & 292.00
panic disorder, ICD 300.01, DSM 300.01 & 300.21
anxiety, ICD 300.02, DSM 300.00
post-traumatic syndrome, DSM 309.89
memory loss, DSM 294.00
dementia of aging, ICD 290
social phobia, ICD 300.23, DSM 300.23
attention deficit hyperactivity disorder, ICD 314.0
disruptive behavior disorders, ICD 312
impulse control disorders, ICD 312, DSM 312.39 & 312.34
borderline personality disorder, ICD 301.83, DSM 301.83
chronic fatigue syndrome
premature ejaculation, DSM 302.75
erectile difficulty, DSM 302.72
anorexia nervosa, ICD 307.1, DSM 307.10
disorders of sleep, ICD 307.4
autism
mutism
trichotillomania Anxiety and its frequent concomitant, panic disorder, may be particularly mentioned in connection with the present compounds. The subject is carefully explained by the Diagnostic and Statistical Manual of Mental Disorders, published by the American Psychiatric Association, which classifies anxiety under its category 300.02.

In addition, the unique combination of pharmacological properties possessed by the compounds of formula I permit those compounds to be used in a method of simultaneously treating anxiety and depression. The anxiety portion of the combined syndrome is believed to be attacked by the 5HT-$1_A$ receptor-affecting property of the compounds, and the depression portion of the condition is believed to be addressed by the serotonin reuptake inhibition property. Thus, administration of an effective amount, which is determined in an analogous manner as discussed hereinabove, of a compound of formula I, will provide a method of simultaneously treating anxiety and depression.

It is well known that the chronic administration of nicotine results in tolerance and, eventually, dependence. The use of tobacco has become extremely widespread in all countries, despite the well known adverse effects of the use of tobacco in all its forms. Thus, it is clear that tobacco use is extremely habit-forming, if not addictive, and that its use provides sensations to the user which are pleasant and welcome, even though the user may be fully aware of the drastic long term ill effects of its use.

Recently, vigorous campaigns against the use of tobacco have taken place, and it is now common knowledge that the cessation of smoking brings with it numerous unpleasant withdrawal symptoms, which include irritability, anxiety, restlessness, lack of concentration, lightheadedness, insomnia, tremor, increased hunger and weight gain, and, of course, a craving for tobacco.

At the present time, probably the most widely used therapy to assist the cessation of tobacco use is nicotine replacement, by the use of nicotine chewing gum or nicotine-providing transdermal patches. It is widely known, however, that nicotine replacement is less effective without habit-modifying psychological treatment and training.

Thus, the present method of preventing or alleviating the symptoms caused by withdrawal or partial withdrawal from the use of tobacco or of nicotine comprises the previously discussed method of affecting the serotonin $1_A$ receptor, in that the treatment method comprises the administration to a patient an effective amount of a compound of formula I. The method of the present invention is broadly useful in assisting persons who want to cease or reduce their use of tobacco or nicotine. Most commonly, the form of tobacco use is smoking, most commonly the smoking of cigarettes. The present invention is also helpful, however, in assisting in breaking the habit of all types of tobacco smoking, as well as the use of snuff, chewing tobacco, etc. The present method is also helpful to those who have replaced, or partially replaced, their use of tobacco with the use of nicotine replacement therapy. Thus, such patients can be assisted to reduce and even eliminate entirely their dependence on nicotine in all forms.

A particular benefit of therapy with the present compounds is the elimination or reduction of the weight gain which very often results from reducing or withdrawing from use of tobacco or nicotine.

It will be understood that the present invention is useful for preventing or alleviating the withdrawal symptoms which afflict patients who are trying to eliminate or reduce their use of tobacco or nicotine. The common withdrawal symptoms of such people include, at least, irritability, anxiety, restlessness, lack of concentration, insomnia, nervous tremor, increased hunger and weight gain, lightheadedness, and the craving for tobacco or nicotine. The prevention or alleviation of such symptoms, when they are caused by or occur in conjunction with ceasing or reducing the patient's use of tobacco or nicotine is a desired result of the present invention and an important aspect thereof.

The invention is carried out by administering an effective amount of a compound of formula I to a patient who is in need of or carrying out a reduction or cessation of tobacco or nicotine use.

As used herein, the term "Patient" refers to a mammal such as a dog, cat, guinea pig, mouse, rat, monkey, or human being. It is understood that a human being is the preferred patient.

As used herein, the terms "treating" or "to treat" each mean to alleviate symptoms, eliminate the causation either on a temporary or permanent basis, or to prevent or slow the appearance of symptoms of the named disorder.

As used herein, the term "effective amount" refers to the amount of a compound of formula (I) which is effective, upon single or multiple dose administration to a patient, in treating the patient suffering from the named disorder. The effective amount of compound to be administered, in general, is from about 1 to about 200 mg/day. The daily dose may be administered in a single bolus, or in divided doses, depending on the judgment of the physician in charge of the case. A more preferred range of doses is from about 5 to about 100 mg/day; other dosage ranges which may be preferred in certain circumstances are from about 10 to about 50 mg/day; from about 5 to about 50 mg/day; from about 10 to about 25 mg/day; and a particularly preferred range is from about 20 to about 25 mg/day.

An effective amount can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

In effecting treatment of a patient afflicted with a condition, disease or disorder described above, a compound of formula (I) can be administered in any form or mode which makes the compound bioavailable in effective amounts, including oral and parenteral routes. For example, compounds of formula (I) can be administered orally, subcutaneously, intramuscularly, intravenously, transdermally, intranasally, rectally, and the like. Oral administration is generally preferred. One skilled in the art of preparing formulations can readily select the proper form and mode of administration depending upon the particular characteristics of the compound selected, the disease state to be treated, the stage of the disease, and other relevant circumstances.

It is understood that, while the compounds of formula I individually provide the benefit of the combination of serotonin reuptake inhibitors and serotonin 1A antagonists, it is entirely possible to administer a compound of formula I in combination with a conventional serotonin reuptake inhibitor in order to obtain still further enhanced results in potentiating serotonin reuptake inhibition. Examples of representative serotonin reuptake inhibitors include but are not limited to the following:

Fluoxetine, N-methyl-3-(p-trifluoromethylphenoxy)-3-phenylpropylamine, is marketed in the hydrochloride salt form, and as the racemic mixture of its two enantiomers. U.S. Pat. No. 4,314,081 is an early reference on the compound. Robertson, et al., *J. Med. Chem.* 31, 1412 (1988), taught the separation of the R and S enantiomers of fluoxetine and showed that their activity as serotonin uptake inhibitors is similar to each other. In this document, the word "fluoxetine" will be used to mean any acid addition salt or the free base, and to include either the racemic mixture or either of the R and S enantiomers.

Duloxetine, N-methyl-3-(1-naphthalenyloxy)-3-(2-thienyl)propanamine, is usually administered as the hydrochloride salt and as the (+) enantiomer. It was first taught by U.S. Pat. No. 4,956,388, which shows its high potency. The word "duloxetine" will be used here to refer to any acid addition salt or the free base of the molecule.

Venlafaxine is known in the literature, and its method of synthesis and its activity as an inhibitor of serotonin and norepinephrine uptake are taught by U.S. Pat. No. 4,761,501. Venlafaxine is identified as compound A in that patent.

Milnacipran (N,N-diethyl-2-aminomethyl-1-phenylcyclopropanecarboxamide) is taught by U.S. Pat. No. 4,478,836, which prepared milnacipran as its Example 4. The patent describes its compounds as antidepressants. Moret, et al., *Neuropharmacology* 24, 1211-19 (1985), describe its pharmacological activities.

Citalopram, 1-[3-(dimethylamino)propyl]-1-(4-fluorophenyl)-1,3-dihydro-5-isobenzofurancarbonitrile, is disclosed in U.S. Pat. No. 4,136,193 as a serotonin reuptake inhibitor. Its pharmacology was disclosed by Christensen, et al., *Eur. J. Pharmacol.* 41, 153 (1977), and reports of its clinical effectiveness in depression may be found in Dufour, et al., *Int. Clin. Psychopharmacol.* 2, 225 (1987), and Timmerman, et al., ibid., 239.

Fluvoxamine, 5-methoxy-1-[4-(trifluoromethyl)phenyl]-1-pentanone-O-(2-aminoethyl)oxime, is taught by U.S. Pat. No. 4,085,225. Scientific articles about the drug have been published by Claassen, et al., *Brit. J. Pharmacol.* 60, 505 (1977); and De Wilde, et al., *J. Affective Disord.* 4, 249 (1982); and Benfield, et al., *Drugs* 32, 313 (1986).

Sertraline, 1-(3,4-dichlorophenyl)-4-methylaminotetralin, is disclosed in U.S. Pat. No. 4,536,518.

Paroxetine, trans-(−)-3-[(1,3-benzodioxol-5-yloxy)methyl]-4-(4-fluorophenyl)piperidine, may be found in U.S.

Pat. Nos. 3,912,743 and 4,007,196. Reports of the drug's activity are in Lassen, *Eur. J. Pharmacol.* 47, 351 (1978); Hassan, et al., *Brit. J. Clin. Pharmacol.* 19, 705 (1985); Laursen, et al., *Acta Psychiat. Scand.* 71, 249 (1985); and Battegay, et al., *Neuropsychobiology* 13, 31 (1985).

All of the U.S. patents which have been mentioned above in connection with compounds used in the present invention are incorporated herein by reference.

Fluoxetine or duloxetine are the preferred SRIs in pharmaceutical compositions combining a compound of formula I and an SRI, and the corresponding methods of treatment.

It will be understood by the skilled reader that all of the compounds used in the present invention are capable of forming salts, and that the salt forms of pharmaceuticals are commonly used, often because they are more readily crystallized and purified than are the free bases. In all cases, the use of the pharmaceuticals described above as salts is contemplated in the description herein, and often is preferred, and the pharmaceutically acceptable salts of all of the compounds are included in the names of them.

The dosages of the drugs used in the present combination must, in the final analysis, be set by the physician in charge of the case, using knowledge of the drugs, the properties of the drugs in combination as determined in clinical trials, and the characteristics of the patient, including diseases other than that for which the physician is treating the patient. General outlines of the dosages, and some preferred human dosages, can and will be provided here. Dosage guidelines for some of the drugs will first be given separately; in order to create a guideline for any desired combination, one would choose the guidelines for each of the component drugs.

Fluoxetine: from about 1 to about 80 mg, once/day; preferred, from about 10 to about 40 mg once/day; preferred for bulimia and obsessive-compulsive disease, from about 20 to about 80 mg once/day;

Duloxetine: from about 1 to about 30 mg once/day; preferred, from about 5 to about 20 mg once/day;

Venlafaxine: from about 10 to about 150 mg once-thrice/day; preferred, from about 25 to about 125 mg thrice/day;

Milnacipran: from about 10 to about 100 mg once-twice/day; preferred, from about 25 to about 50 mg twice/day;

Citalopram: from about 5 to about 50 mg once/day; preferred, from about 10 to about 30 mg once/day;

Fluvoxamine: from about 20 to about 500 mg once/day; preferred, from about 50 to about 300 mg once/day;

Paroxetine: from about 5 to about 100 mg once/day; preferred, from about 50 to about 300 mg once/day.

In more general terms, one would create a combination of the present invention by choosing a dosage of SRI according to the spirit of the above guideline, and choosing a dosage of the compound of formula I in the ranges taught above.

The adjunctive therapy of the present invention is carried out by administering a SRI together with a compound of formula I in any manner which provides effective levels of the two compounds in the body at the same time. All of the compounds concerned are orally available and are normally administered orally, and so oral administration of the adjunctive combination is preferred. They may be administered together, in a single dosage form, or may be administered separately.

However, oral administration is not the only route or even the only preferred route. For example, transdermal administration may be very desirable for patients who are forgetful or petulant about taking oral medicine. One of the drugs may be administered by one route, such as oral, and the other may be administered by the trans-dermal, percutaneous, intravenous, intramuscular, intranasal or intrarectal route, in particular circumstances. The route of administration may be varied in any way, limited by the physical properties of the drugs and the convenience of the patient and the caregiver.

It is particularly preferred, however, for the adjunctive combination to be administered as a single pharmaceutical composition, and so pharmaceutical compositions incorporating both a SRI and a compound of formula I are important embodiments of the present invention. Such compositions may take any physical form which is pharmaceutically acceptable, but orally usable pharmaceutical compositions are particularly preferred. Such adjunctive pharmaceutical compositions contain an effective amount of each of the compounds, which effective amount is related to the daily dose of the compounds to be administered. Each adjunctive dosage unit may contain the daily doses of both compounds, or may contain a fraction of the daily doses, such as one-third of the doses. Alternatively, each dosage unit may contain the entire dose of one of the compounds, and a fraction of the dose of the other compound. In such case, the patient would daily take one of the combination dosage units, and one or more units containing only the other compound. The amounts of each drug to be contained in each dosage unit depends on the identity of the drugs chosen for the therapy, and other factors such as the indication for which the adjunctive therapy is being given.

As stated above, the benefit of the adjunctive therapy is its ability to augment the increase in availability of serotonin, norepinephrine and dopamine caused by the SRI compounds, resulting in improved activity in treating the various conditions described below in detail. The increase in availability of serotonin is particularly important and is a preferred aspect of the invention. Further, the invention provides a more rapid onset of action than is usually provided by treatment with the SRI alone.

Pharmaceutical Compositions

The present invention provides pharmaceutical compositions of compounds of formula I, including the hydrates thereof, comprising, as an active ingredient, a compound of formula I in admixture or otherwise in association with one or more pharmaceutically acceptable carriers, diluents or excipients. It is customary to formulate pharmaceuticals for administration, to provide control of the dosage and stability of the product in shipment and storage, and the usual methods of formulation are entirely applicable to the compounds of formula I. Such pharmaceutical compositions are valuable and novel because of the presence of the compounds of formula I therein. Although pharmaceutical chemists are well aware of many effective ways to formulate pharmaceuticals, which technology is applicable to the present compounds, some discussion of the subject will be given here for the convenience of the reader.

The usual methods of formulation used in pharmaceutical science and the usual types of compositions may be used according to the present invention, including tablets, chewable tablets, capsules, solutions, parenteral solutions, intranasal sprays or powders, troches, suppositories, transdermal patches and suspensions. In general, pharmaceutical compositions contain from about 0.5% to about 50% of the compound of formula (I) in total, depending on the desired dose and the type of composition to be used. The amount of the compound of formula (I), however, is best defined as the effective amount, that is, the amount of each compound which provides the desired dose to the patient in need of such treatment. The activity of the compounds do not depend on the nature of the composition, so the compositions are chosen and formulated solely for convenience and economy. Any compound may be formulated in any desired form of composition. Some discussion of different compositions will be provided, followed by some typical formulations.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acidic contents of the stomach. Such formulations are created by coating a solid dosage form with a film of a polymer which is insoluble in acidic environments, and soluble in basic environments. Exemplary films are cellulose acetate phthalate, polyvinyl acetate phthalate, hydroxypropyl methylcellulose phthalate and hydroxypropyl methylcellulose acetate succinate.

Tablets are often coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

When it is desired to administer the combination as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with pores through which the drugs are pumped by osmotic action.

The following typical formulae are provided for the interest and information of the pharmaceutical scientist.

Formulation 1

Hard gelatin capsules are prepared using the following ingredients:

|  | Quantity (mg/capsule) |
| --- | --- |
| Example #1 | 20 mg |
| Starch, dried | 200 mg |
| Magnesium stearate | 10 mg |
| Total | 230 mg |

As with any group of structurally related compounds which possess a particular generic utility, certain groups and configurations are preferred for compounds of formula I or formula Ia.

With respect to substituent $R^1$, compounds wherein $R^1$ is hydrogen, F, methyl, ethyl, —C(=O)NR$^8$R$^9$, or CN are preferred, with hydrogen, methyl, and —C(=O)NH$_2$ being especially preferred.

With respect to substitunet $R^2$, compounds wherein $R^2$ is hydrogen are preferred.

With respect to substituent A, compounds wherein A is hydroxy are preferred.

In addition, it is further preferred that when A is hydroxy, it is in the (S)-configuration.

With respect to substituent m, compounds wherein m is 1 or 2 are preferred.

With respect to substituent n, compounds wherein n is 1 or 2 are preferred.

With respect to substituents p and q, compounds wherein p and q are both one are preferred.

With respect to substituent X, compounds wherein X is hydrogen are preferred.

With respect to Y, compounds wherein Y is S are preferred.

With respect to substituent $R^3$, compounds wherein $R^3$ is hydrogen, methyl, ethyl or propyl are preferred.

With respect to substituent $R^4$, compounds wherein $R^4$ is hydrogen, methyl, ethyl or propyl are preferred.

With respect to substituent $R^5$, compounds wherein $R^5$ is hydrogen, F, Cl, Br, I OH, $C_{1-C6}$ alkyl, $C_{1-C6}$ alkoxy, halo($C_{1-C6}$) alkyl, phenyl, substituted phenyl, C(=O)NR$_8$R$_9$, NO$_2$, NH$_2$, and CN are preferred, with hydrogen, F, Cl, Br, methyl, ethyl, propyl, isopropyl, methoxy, ethoxy, propoxy and isopropoxy being especially preferred.

With respect to substituent $R^6$, compounds wherein $R^6$ is hydrogen, F, Cl, Br, I OH, $C_{1-C6}$ alkyl, $C_{1-C6}$ alkoxy, halo($C_{1-C6}$) alkyl, phenyl, substituted phenyl, C(=O)NR$_8$R$_9$, NO$_2$, NH$_2$, and CN are preferred, with hydrogen, F, Cl, Br, methyl, ethyl, propyl, isopropyl, methoxy, ethoxy, propoxy and isopropoxy being especially preferred.

With respect to substituent $R^7$, compounds wherein $R^7$ is hydrogen, F, Cl, Br, methyl, ethyl, propyl, isopropyl or butyl are preferred, with methyl, ethyl, and propyl being especially preferred.

With respect to substituent $R^8$, compounds wherein $R^8$ is hydrogen, methyl, ethyl, propyl, isopropyl or butyl are preferred.

With respect to substituent $R^9$, compounds wherein $R^9$ is hydrogen, methyl, ethyl, propyl, isopropyl or butyl are preferred.

With respect to the piperidine portion of formula I, compounds with the following substitutions are preferred:

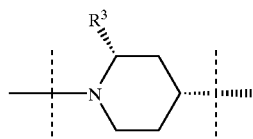
(a)

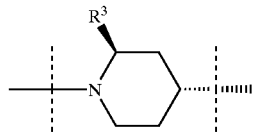
(b)

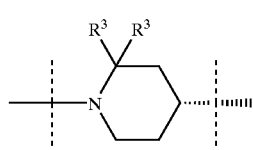
(c)

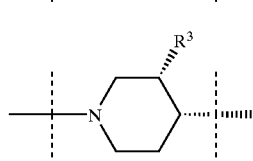
(d)

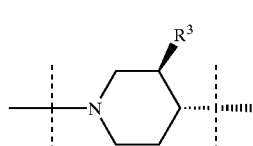
(e)

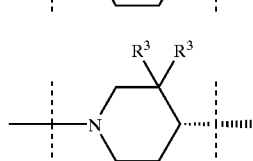
(f)

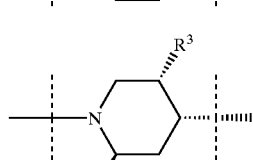
(g)

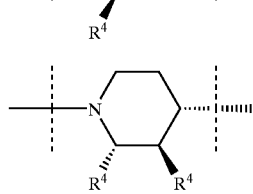
(h)

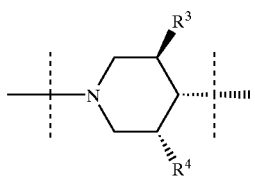
(i)

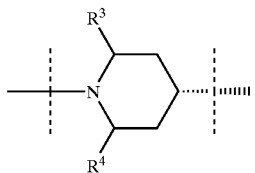
(j)

including the individual enantiomers thereof.

With respect to substituent B, compounds with the following substitutions are preferred:

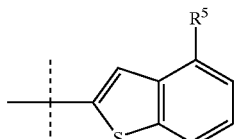
(a)

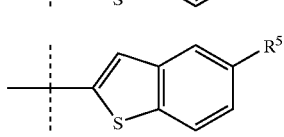
(b)

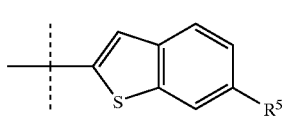
(c)

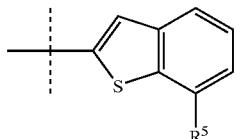
(d)

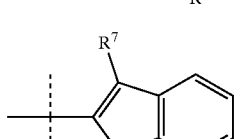
(e)

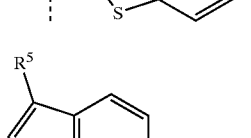
(f)

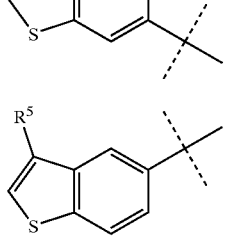
(g)

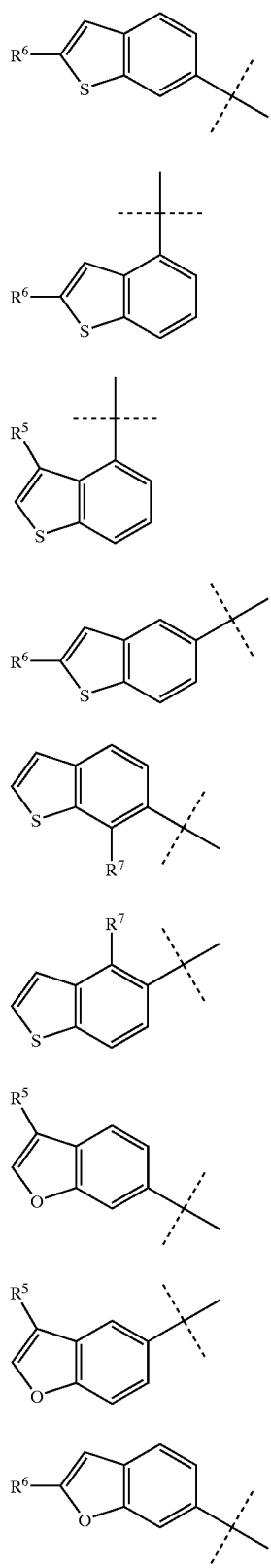
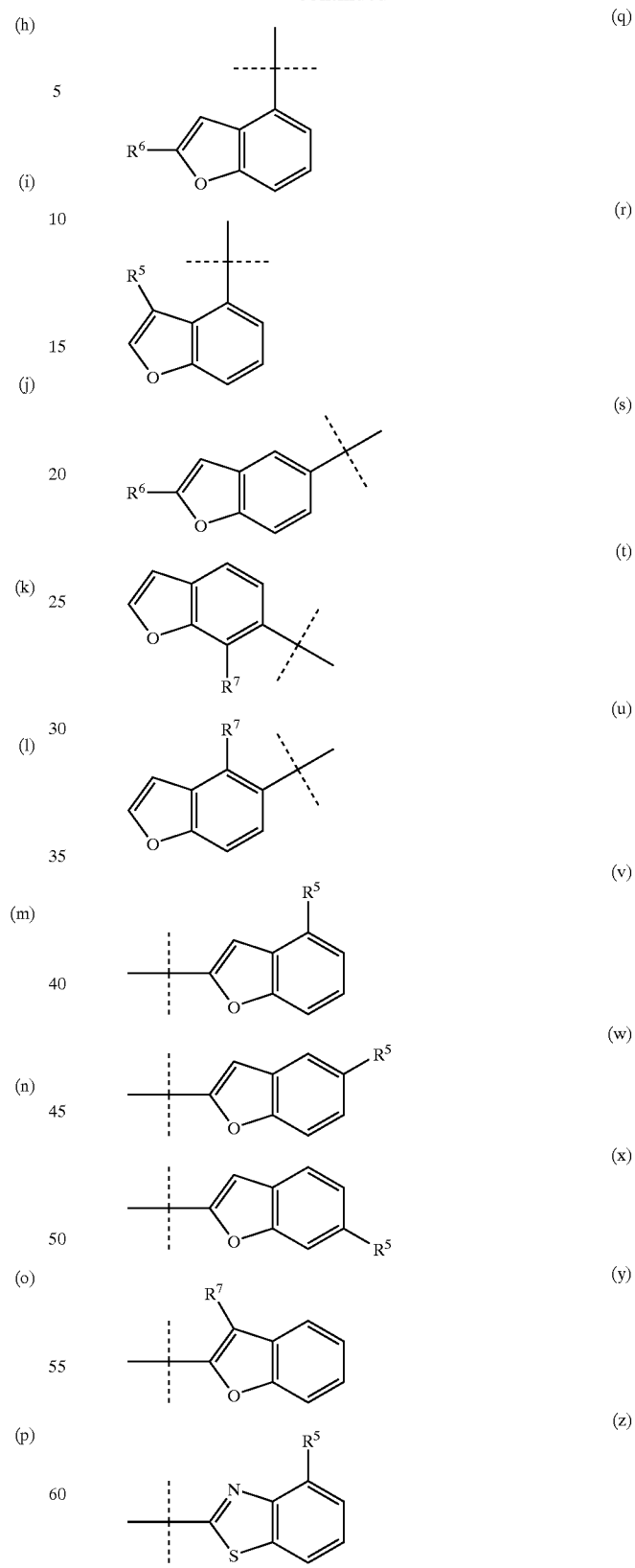

-continued
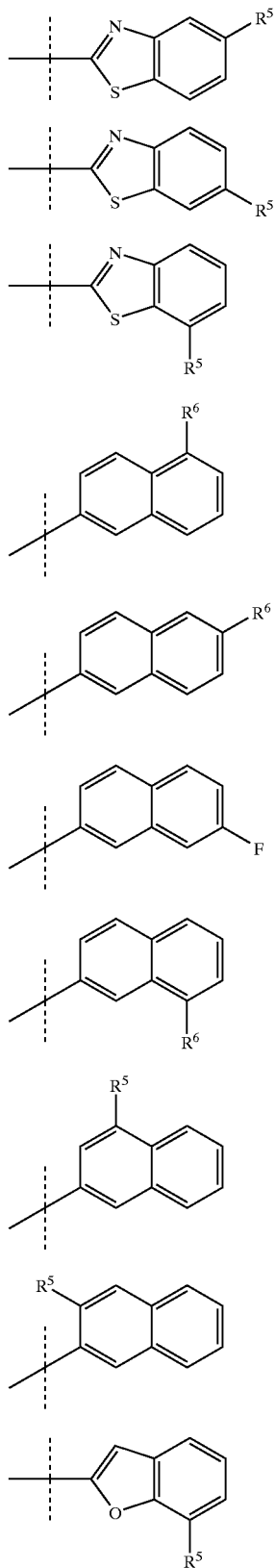
(aa)
(bb)
(cc)
(dd)
(ee)
(ff)
(gg)
(hh)
(ii)
(jj)
More specifically, as shown in Table 1, the following substituents represented by B are especially preferred:
TABLE I
| | Substituent B | |
|---|---|---|
| A | 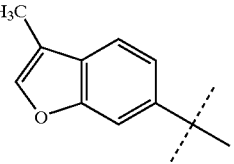 | |
| B | 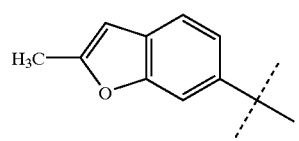 | |
| C | 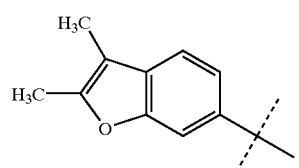 | |
| D | 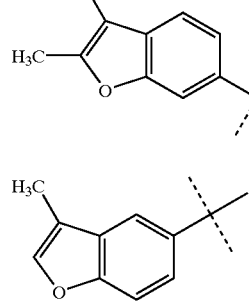 | |
| E | 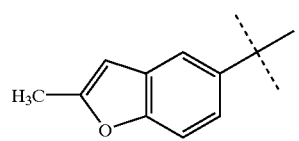 | |
| F | 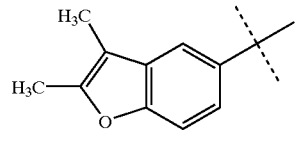 | |
| G | 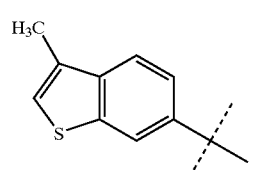 | |
| h | 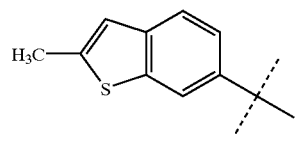 | |
| i | 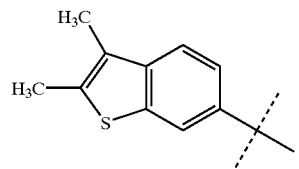 | |

TABLE I-continued
| Substituent B | | |
|---|---|---|
| j | 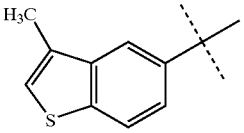 | |
| k | 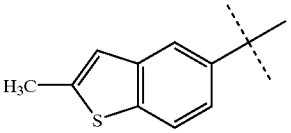 | |
| l | 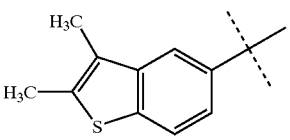 | |
| m | 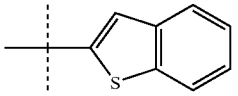 | |
| n | 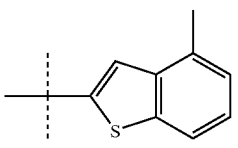 | |
| o | 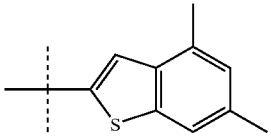 | |
| p | 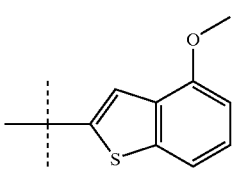 | |
| q | 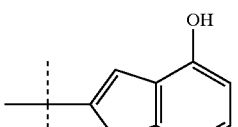 | |
| r | 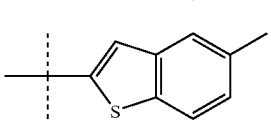 | |
| s | 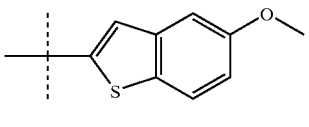 | |
| t | 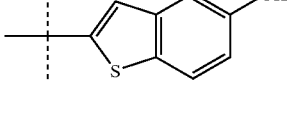 | |
TABLE I-continued
| Substituent B | | |
|---|---|---|
| u | 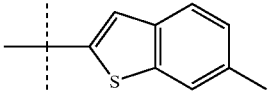 | |
| v | 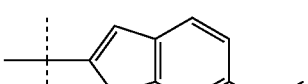 | |
| w | 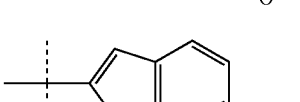 | |
| x | 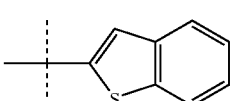 | |
| y | 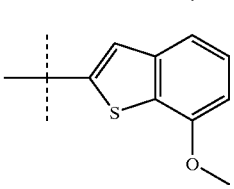 | |
| z | 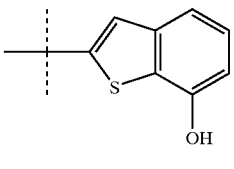 | |
| aa | 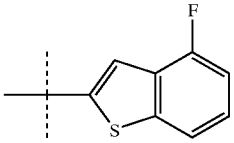 | |
| bb | 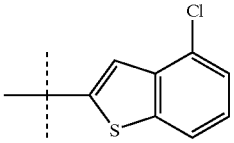 | |
| cc | 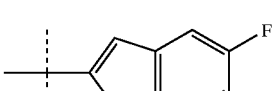 | |
| dd | 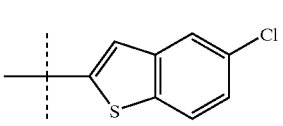 | |
| ee | 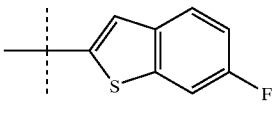 | |

TABLE I-continued
| | Substituent B |
|---|---|
| ff | 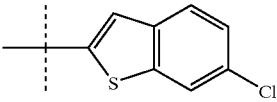 |
| gg | 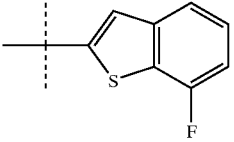 |
| hh | 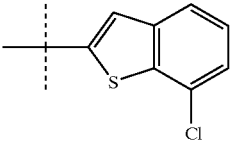 |
| ii | 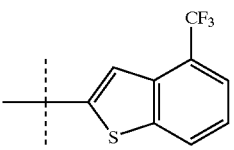 |
| jj | 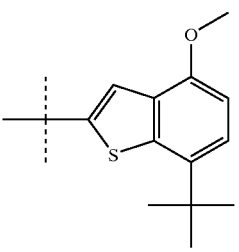 |
| kk | 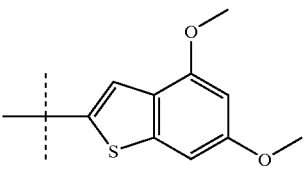 |
| ll | 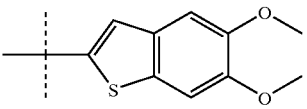 |
| mm | 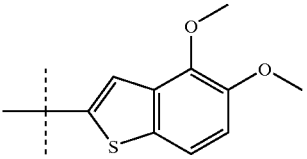 |
| nn | 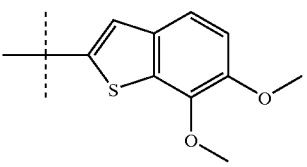 |
| oo | 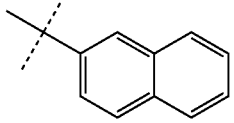 |
| pp | 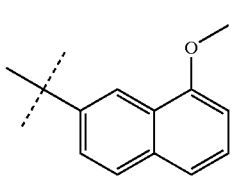 |
| qq | 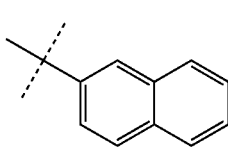 |
| rr | 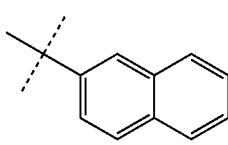 |
| tt | 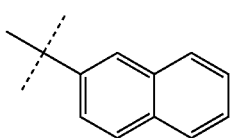 |
| uu | 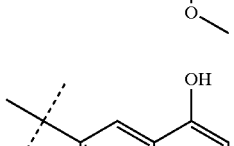 |
| vv | 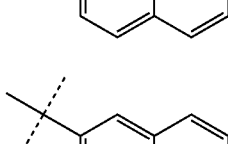 |
| ww | 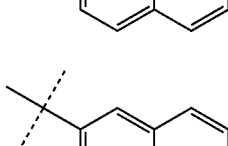 |
| xx | 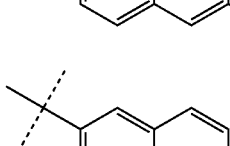 |

We claim:
1. A compound of the formula:

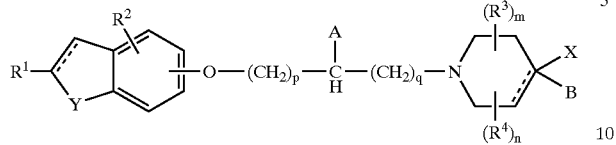

wherein

A is hydrogen, OH or (C$_1$–C$_6$) alkoxy:

B is selected from the group consisting of:

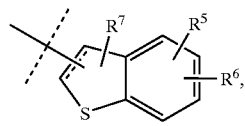

(a)

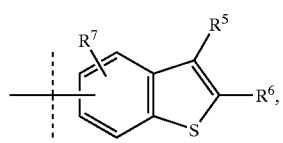

(b)

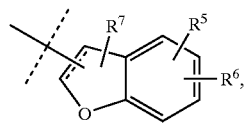

(c)

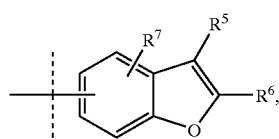

(d)

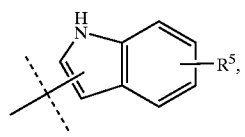

(e)

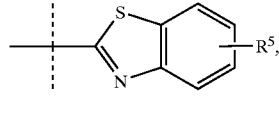

(f)

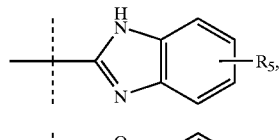

(g)

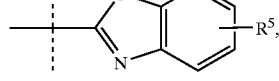

(h)

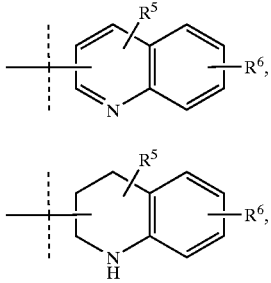

(i)

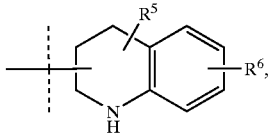

(j)

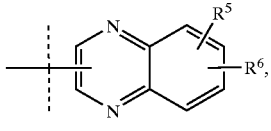

(k)

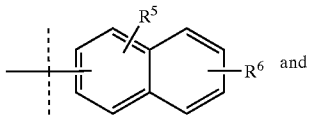

(l)

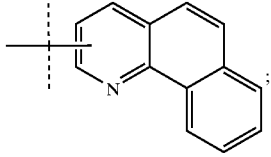

(m)

▬ represents a single or a double bond;

X is hydrogen, OH or C$_1$–C$_6$ alkoxy when ▬ represents a single bond in the piperidine ring, and X is nothing when ▬ represents a double bond in the piperidine ring;

Y is S or CH$_2$;

R$^1$ is hydrogen, F, C$_1$–C$_{20}$ alkyl, —C(=O)NR$^8$R$^9$, or CN;

R$^2$ is hydrogen, F, Cl, Br, I, OH, C$_1$–C$_6$ alkyl or C$_1$–C$_6$ alkoxy;

R$^3$ and R$^4$ are each independently hydrogen or C$_1$–C$_4$ alkyl;

R$^5$ and R$^6$ are each independently hydrogen, F, Cl, Br, I, OH, C$_1$–C$_6$ alkyl, C$_1$–C$_6$ alkoxy, halo(C$_1$–C$_6$)alkyl, phenyl, —C(=O)NR$^8$R$^9$, NO$_2$, NH$_2$, CN, or phenyl substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, NO$_2$, NH$_2$, CN, and phenyl;

R$^7$ is hydrogen, F, Cl, Br, I, OH, C$_1$–C$_6$ alkyl or (C$_1$–C$_6$ alkyl)NR$^8$R$^9$;

R$^8$ and R$^9$ are each independently hydrogen or C$_1$–C$_{10}$ alkyl;

m is 0, 1, or 2;

n is 0, 1, or 2;

p is 0, 1, 2, 3 or 4; and q is 0, 1, 2 or 3; or a pharmaceutically acceptable salt thereof.

2. A compound of the formula:

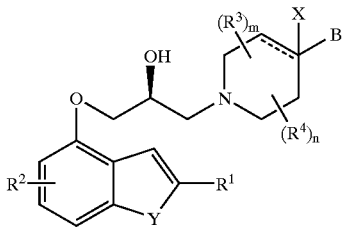

wherein

B is selected from the group consisting of:

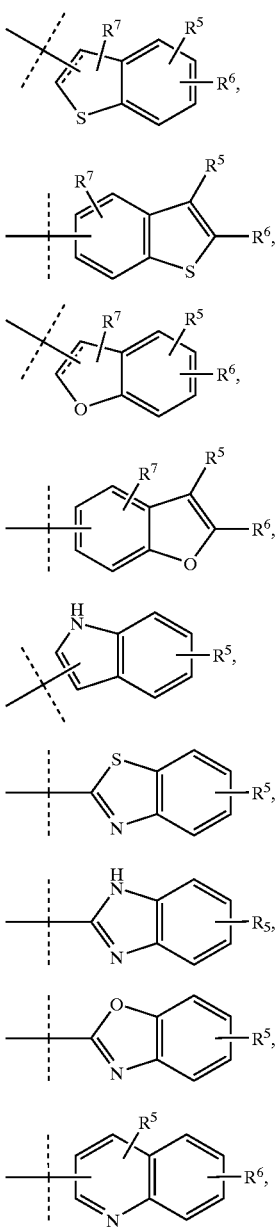

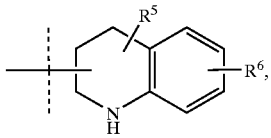

(j)

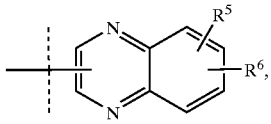

(k)

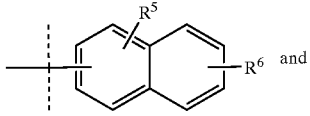

(l) and

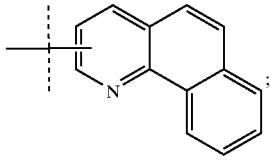

(m);

⎯⎯ represents a single or a double bond;

X is hydrogen, OH or $C_1$–$C_6$ alkoxy when ⎯⎯ represents a single bond in the piperidine ring, and X is nothing when ⎯⎯ represents a double bond in the piperidine ring;

Y is S or $CH_2$;

$R^1$ is hydrogen, F, $C_1$–$C_{20}$ alkyl, —C(=O)$NR^8R^9$, or CN;

$R^2$ is hydrogen, F, Cl, Br, I, OH, $C_1$–$C_6$ alkyl or $C_1$–$C_6$ alkoxy;

$R^3$ and $R^4$ are each independently hydrogen or $C_1$–$C_4$ alkyl;

$R^5$ and $R^6$ are each independently hydrogen, F, Cl, Br, I, OH, $C_1$–$C_6$ alkyl, $C_1$–$C_6$ alkoxy, halo($C_1$–$C_6$)alkyl, phenyl, —C(=O)$NR^8R^9$, $NO_2$, $NH_2$, CN, or phenyl substituted with from 1 to 3 substituents selected from the group consisting of F, Cl, Br, I, OH, $C_1$–$C_6$ alkyl, $C_1$–$C_6$ alkoxy, halo($C_1$–$C_6$)alkyl, $NO_2$, $NH_2$, CN, and phenyl;

$R^7$ is hydrogen, F, Cl, Br, I, OH, $C_1$–$C_6$ alkyl or ($C_1$–$C_6$ alkyl)$NR^8R^9$;

$R^8$ and $R^9$ are each independently hydrogen or $C_1$–$C_{10}$ alkyl;

m is 0, 1, or 2; and n is 0, 1, or 2; or a pharmaceutically acceptable salt thereof.

3. A compound according to claim 2 wherein Y is S.

4. A compound according to claim 3 wherein $R^2$ is hydrogen.

5. A compound according to claim 2 Wherein $R^1$ is hydrogen, methyl, or —C(=O)$NH_2$.

6. A compound according to claim 2 wherein X is hydrogen.

7. A compound according to claim 2 wherein $R^1$ is hydrogen or methyl.

8. A compound according to claim 2 wherein m is 0 and n is 1.

9. A compound according to claim 2 wherein $R^3$ is hydrogen and $R^4$ is methyl.

10. A compound according to claim 2 wherein m is 0 and n is 0.

11. A compound according to claim 2 wherein B is:

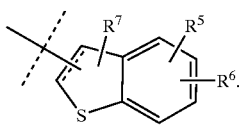

12. A compound according to claim 11 wherein $R^7$ is methyl, ethyl, or propyl, and $R^5$ and $R^6$ are hydrogen.

13. A method of inhibiting the reuptake of serotonin and antagonizing the 5-HT$_{1A}$ receptor which comprises administering to a patient in need of such treatment an effective amount of a compound of the formula:

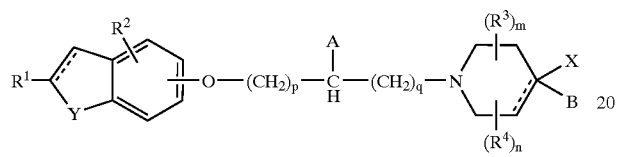

wherein

A is hydrogen or OH:

B is selected from the group consisting of:

(a) 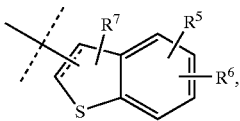

(b) 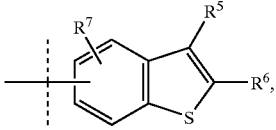

(c) 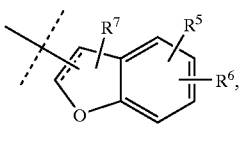

(d) 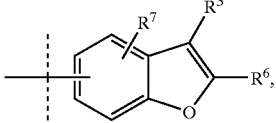

(e) 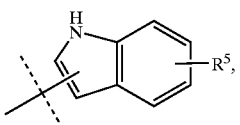

(f) 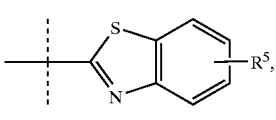

(g) 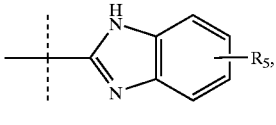

(h) 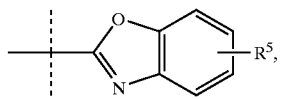

(i) 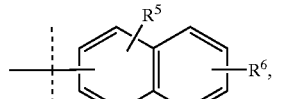

(j) 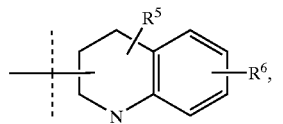

(k) 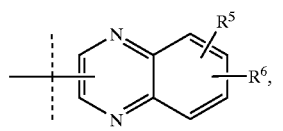

(l) 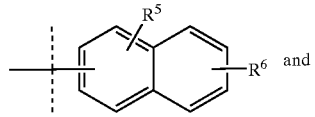 and (m) 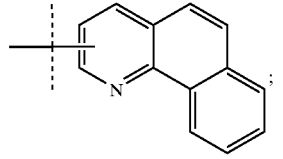;

━━━ represents a single or a double bond;

X is hydrogen, OH or $C_1$–$C_6$ alkoxy when ━━━ represents a single bond in the piperidine ring, and X is nothing when ━━━ represents a double bond piperidine ring;

$R^1$ is hydrogen, F, $C_1$–$C_{20}$ alkyl, —C(=O)NR$^8$R$^9$, or CN;

$R^2$ is hydrogen, F, Cl, Br, I, OH, $C_1$–$C_6$ alkyl or $C_1$–$C_6$ alkoxy;

$R^3$ and $R^4$ are each independently hydrogen or $C_1$–$C_4$ alkyl;

$R^5$ and $R^6$ are each independently hydrogen, F, Cl, Br, I, OH, $C_1$–$C_6$ alkyl, $C_1$–$C_6$ alkoxy, halo($C_1$–$C_6$)alkyl, phenyl, —C(=O)NR$^8$R$^9$, NO$_2$, NH$_2$, CN, or phenyl substituted with from 1 to 3 substituents selected from the group consisting of F, Cl, Br, I, OH, $C_1$–$C_6$ alkyl, $C_1$–$C_6$ alkoxy, halo($C_1$–$C_6$)alkyl, NO$_2$, NH$_2$, CN, and phenyl;

$R^7$ is hydrogen, F, Cl, Br, I, OH, $C_1$–$C_6$ alkyl or ($C_1$–$C_6$ alkyl)NR$^8$R$^9$;

$R^8$ and $R^9$ are each independently hydrogen or $C_1$–$C_{10}$ alkyl;

m is 0, 1, or 2;

n is 0, 1, or 2;

p is 0, 1, 2, 3 or 4; and q is 0, 1, 2 or 3; or a pharmaceutically acceptable salt thereof;

with the proviso that if both $R^3$ and $R^4$ represent hydrogen, then $R^1$ is F, $C_1$–$C_{20}$ alkyl, —C(=O)NR$^8$R$^9$, or CN.

14. A method of potentiating the action of a serotonin reuptake inhibitor comprising administering to a patient in of such treatment a compound formula:

(structure shown)

wherein

A is hydrogen or OH:

B is selected from the group consisting of:

(a) (thiophene-fused structure with $R^7$, $R^5$, $R^6$)

(b) (benzothiophene structure with $R^7$, $R^5$, $R^6$)

(c) (benzofuran structure with $R^7$, $R^5$, $R^6$)

(d) (benzofuran structure with $R^7$, $R^5$, $R^6$)

(e) (indole structure with $R^7$, $R^5$)

(f) (benzothiazole structure with $R^5$)

(g) (benzimidazole structure with $R_5$)

(h) (benzoxazole structure with $R^5$)

(i) (quinoline structure with $R^5$, $R^6$)

(j) (tetrahydroquinoline structure with $R^5$, $R^6$)

(k) (quinoxaline structure with $R^5$, $R^6$)

(l) (naphthalene structure with $R^5$, $R^6$) and (m) (benzoquinoline structure);

▬ represents a single or a double bond;

X is hydrogen, OH or $C_1$–$C_6$ alkoxy when ▬ represents a single bond in the piperidine ring, and X is nothing when ▬ represents a double bond piperidine ring;

$R^1$ is hydrogen, F, $C_1$–$C_{20}$ alkyl, —C(=O)NR$^8$R$^9$, or CN;

$R^2$ is hydrogen, F, Cl, Br, I, OH, $C_4$–$C_6$ alkyl or $C_1$–$C_6$ alkoxy;

$R^3$ and $R^1$ are each independently hydrogen or $C_1$–$C_4$ alkyl;

$R^5$ and $R^6$ are each independently hydrogen, F, Cl, Br, I, OH, $C_1$–$C_6$ alkyl, $C_1$–$C_6$ alkoxy, halo($C_1$–$C_6$)alkyl, phenyl, —C(=O)NR$^8$R$^9$, $NO_2$, $NH_2$, CN, or phenyl substituted with from 1 to 3 substituents selected from the group consisting of F, Cl, Br, I, OH, $C_1$–$C_6$ alkyl, $C_1$–$C_6$ alkoxy, halo($C_1$–$C_6$)alkyl, $NO_2$, $NH_2$, CN, and phenyl;

$R^7$ is hydrogen, F, Cl, Br, I, OH, $C_1$–$C_6$ alkyl or ($C_1$–$C_6$ alkyl)NR$^8$R$^9$;

$R^8$ and $R^9$ are each independently hydrogen or $C_1$–$C_{10}$ alkyl;

m is 0, 1, or 2;

n is 0, 1, or 2;

p is 0, 1, 2, 3 or 4; and q is 0, 1, 2 or 3; or a pharmaceutically acceptable salt thereof;

with the proviso that if both $R^3$ and $R^4$ represent hydrogen, then $R^1$ is F, $C_1$–$C_{20}$ alkyl, —C(=O)NR$^8$R$^9$, or CN.

15. A method of treating depression comprising administering to a patient in need thereof an effective amount of a compound of formula:

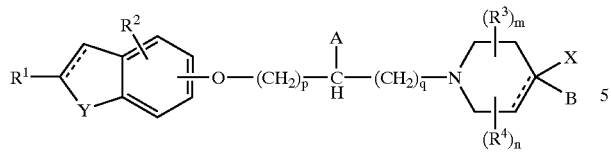

wherein

A is hydrogen or OH;

B is selected from the group consisting of:

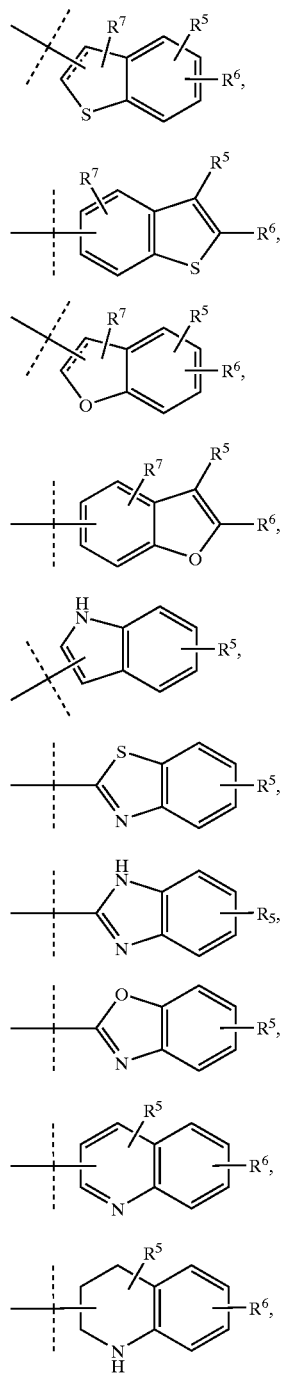

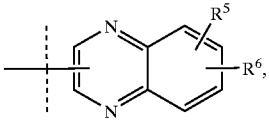

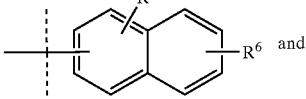

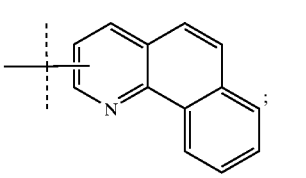

▬▬▬ represents a single or a double bond;

X is hydrogen, OH or $C_1$–$C_6$ alkoxy when ▬▬▬ represents a single bond in the piperidine ring, and X is nothing when ▬▬▬ represents a double bond piperidine ring;

$R^1$ is hydrogen, F, $C_1$–$C_{20}$ alkyl, —C(=O)NR$^8$R$^9$, or CN;

$R^2$ is hydrogen, F, Cl, Br, I, OH, $C_1$–$C_6$ alkyl or $C_1$–$C_6$ alkoxy;

$R^3$ and $R^4$ are each independently hydrogen or $C_1$–$C_4$ alkyl;

$R^5$ and $R^6$ are each independently hydrogen, F, Cl, Br, I, OH, $C_1$–$C_6$ alkyl, $C_1$–$C_6$ alkoxy, halo($C_1$–$C_6$)alkyl, phenyl, —C(=O)NR$^8$R$^9$, NO$_2$, NH$_2$, CN, or phenyl substituted with from 1 to 3 substituents selected from the group consisting of F, Cl, Br, I, OH, $C_1$–$C_6$ alkyl, $C_1$–$C_6$ alkoxy, halo($C_1$–$C_6$)alkyl, NO$_2$, NH$_2$, CN, and phenyl;

$R^7$ is hydrogen, F, Cl, Br, I, OH, $C_1$–$C_6$ alkyl or ($C_1$–$C_6$ alkyl)NR$^8$R$^9$;

$R^8$ and $R^9$ are each independently hydrogen or $C_1$–$C_{10}$ alkyl;

m is 0, 1, or 2;

n is 0, 1, or 2;

p is 0, 1, 2, 3 or 4; and q is 0, 1, 2 or 3; or a pharmaceutically acceptable salt thereof;

with the proviso that if both $R^3$ and $R^4$ represent hydrogen, then $R^1$ is F, $C_1$–$C_{20}$ alkyl, —C(=O)NR$^8$R$^9$, or CN.

16. A pharmaceutical composition comprising an effective amount of a compound according claim 1 in combination with a pharmaceutically acceptable carrier, diluent or excipient.

* * * * *